United States Patent
Rivera et al.

(10) Patent No.: US 11,931,270 B2
(45) Date of Patent: Mar. 19, 2024

(54) PROSTHETIC DIGIT ACTUATOR

(71) Applicant: Touch Bionics Limited, Livingston (GB)

(72) Inventors: Rodrigo Mercader Rivera, Livingston (GB); Hugh Gill, Paisley (GB)

(73) Assignee: Touch Bionics Limited, Livingston (GB)

( * ) Notice: Subject to any disclaimer, the term of this patent is extended or adjusted under 35 U.S.C. 154(b) by 0 days.

(21) Appl. No.: 17/098,045

(22) Filed: Nov. 13, 2020

(65) Prior Publication Data
US 2021/0145610 A1    May 20, 2021

Related U.S. Application Data

(60) Provisional application No. 63/064,614, filed on Aug. 12, 2020, provisional application No. 62/935,852, filed on Nov. 15, 2019.

(51) Int. Cl.
*A61F 2/58* (2006.01)
*A61F 2/68* (2006.01)

(52) U.S. Cl.
CPC ............... *A61F 2/586* (2013.01); *A61F 2/68* (2013.01); *A61F 2002/587* (2013.01); *A61F 2002/6836* (2013.01)

(58) Field of Classification Search
CPC ..................................................... A61F 2/586
See application file for complete search history.

(56) References Cited

U.S. PATENT DOCUMENTS

| | | | |
|---|---|---|---|
| 760,102 | A | 5/1904 | Carnes |
| 1,253,823 | A | 1/1918 | Hobbs |
| 1,507,682 | A | 9/1924 | Pecorella et al. |
| 1,507,683 | A | 9/1924 | Pecorella et al. |
| 2,445,711 | A | 7/1948 | Fitch |
| 2,477,463 | A | 7/1949 | Otterman |
| 2,482,555 | A | 9/1949 | Otterman |

(Continued)

FOREIGN PATENT DOCUMENTS

| | | |
|---|---|---|
| CN | 1803413 | 7/2006 |
| CN | 204274727 | 4/2015 |

(Continued)

OTHER PUBLICATIONS

Invitation to Pay Additional Fees in Application No. PCT/IB2020/060724, dated Feb. 9, 2021.

(Continued)

*Primary Examiner* — Jacqueline Woznicki
(74) *Attorney, Agent, or Firm* — Knobbe, Martens, Olson & Bear, LLP

(57) ABSTRACT

Features for a prosthetic digit actuator. The various systems and methods allow for smaller volume actuators, which in turn allows for smaller digits and/or more space for other features of the digit. The actuator includes a motor that causes rotation of a worm gear along a fixed worm wheel. The worm gear is unibody with the output shaft. The worm gear climbs along the worm wheel to cause rotation of a digit or digit segment. The arrangement of the actuator parts allows for transmitting axial forces in first and second directions corresponding respectively to performing opening and closing rotations of the digits.

20 Claims, 13 Drawing Sheets

(56) References Cited

U.S. PATENT DOCUMENTS

| | | | |
|---|---|---|---|
| 2,508,156 A | 5/1950 | Gillman | |
| 2,516,791 A | 7/1950 | Motis et al. | |
| 2,549,716 A | 4/1951 | Simpson | |
| 2,586,293 A | 2/1952 | Birkigt | |
| 2,592,842 A | 4/1952 | Alderson | |
| 2,669,727 A | 2/1954 | Opuszenski | |
| 2,983,162 A | 5/1961 | Musser | |
| 3,406,584 A | 10/1968 | Roantree | |
| 3,509,583 A | 5/1970 | Fraioli | |
| 3,582,857 A | 6/1971 | Kishel | |
| 3,641,832 A | 2/1972 | Shigeta et al. | |
| 3,683,423 A | 8/1972 | Crapanzano | |
| 3,700,845 A * | 10/1972 | Jonsson | F16C 19/166 384/569 |
| 3,751,995 A | 8/1973 | Carlson | |
| 3,837,010 A | 9/1974 | Prout | |
| 3,866,246 A | 2/1975 | Seamone et al. | |
| 3,883,900 A | 5/1975 | Jerard et al. | |
| 3,922,930 A | 12/1975 | Fletcher et al. | |
| 3,983,936 A * | 10/1976 | Kennard | E21B 29/12 166/361 |
| 4,030,141 A | 6/1977 | Graupe | |
| 4,044,274 A | 8/1977 | Ohm | |
| 4,084,267 A | 4/1978 | Zadina | |
| 4,094,016 A | 6/1978 | Eroyan | |
| 4,114,464 A | 9/1978 | Schubert et al. | |
| 4,197,592 A | 4/1980 | Klein | |
| 4,398,110 A | 8/1983 | Flinchbaugh et al. | |
| 4,558,704 A | 12/1985 | Petrofsky | |
| 4,565,457 A * | 1/1986 | Flander | F16C 33/585 384/615 |
| 4,577,127 A | 3/1986 | Ferree et al. | |
| 4,623,354 A | 11/1986 | Childress et al. | |
| 4,660,702 A * | 4/1987 | Flotow | F16D 23/14 192/109 R |
| 4,678,952 A | 7/1987 | Peterson et al. | |
| 4,808,187 A | 2/1989 | Patterson et al. | |
| 4,813,303 A | 3/1989 | Beezer et al. | |
| 4,822,238 A | 4/1989 | Kwech | |
| 4,946,380 A | 8/1990 | Lee | |
| 4,955,918 A | 9/1990 | Lee | |
| 4,960,425 A | 10/1990 | Yan et al. | |
| 4,990,162 A | 2/1991 | LeBlanc et al. | |
| 5,020,162 A | 6/1991 | Kersten et al. | |
| 5,062,673 A | 11/1991 | Mimura | |
| 5,088,125 A | 2/1992 | Ansell et al. | |
| 5,133,775 A | 7/1992 | Chen | |
| 5,246,463 A | 9/1993 | Giampapa | |
| 5,252,102 A | 10/1993 | Singer et al. | |
| 5,387,245 A | 2/1995 | Fay et al. | |
| 5,413,611 A | 5/1995 | Haslam, II et al. | |
| 5,498,472 A | 3/1996 | Gold | |
| 5,501,498 A | 3/1996 | Ulrich | |
| 5,581,166 A | 12/1996 | Eismann et al. | |
| 5,605,071 A | 2/1997 | Buchanan, Jr. | |
| 5,785,960 A | 7/1998 | Rigg et al. | |
| 5,851,194 A | 12/1998 | Fratrick | |
| 5,852,675 A | 12/1998 | Matsuo et al. | |
| 5,888,213 A | 3/1999 | Sears et al. | |
| 5,888,246 A | 3/1999 | Gow | |
| 6,111,973 A | 8/2000 | Holt et al. | |
| 6,175,962 B1 | 1/2001 | Michelson | |
| 6,223,615 B1 | 5/2001 | Huck | |
| 6,244,873 B1 | 6/2001 | Hill et al. | |
| 6,344,062 B1 | 2/2002 | Abboudi et al. | |
| 6,361,570 B1 | 3/2002 | Gow | |
| 6,517,132 B2 | 2/2003 | Matsuda et al. | |
| 6,591,707 B2 | 7/2003 | Torii et al. | |
| 6,660,043 B2 | 12/2003 | Kajitani et al. | |
| 6,786,112 B2 | 9/2004 | Ruttor | |
| 6,809,440 B2 | 10/2004 | Peterreins | |
| 6,867,516 B2 | 3/2005 | Frey et al. | |
| 6,896,704 B1 | 5/2005 | Higuchi et al. | |
| 6,908,489 B2 | 6/2005 | Didrick | |
| 6,918,622 B2 | 7/2005 | Kim et al. | |
| 7,144,430 B2 | 12/2006 | Archer et al. | |
| 7,243,569 B2 | 7/2007 | Takahashi et al. | |
| 7,316,304 B2 | 1/2008 | Heravi et al. | |
| 7,316,795 B1 | 1/2008 | Knauss | |
| 7,370,896 B2 | 5/2008 | Anderson et al. | |
| 7,481,782 B2 | 1/2009 | Scott et al. | |
| 7,640,680 B1 | 1/2010 | Castro | |
| 7,655,051 B2 | 2/2010 | Stark | |
| 7,823,475 B2 | 11/2010 | Hirabayashi et al. | |
| 7,867,287 B2 | 1/2011 | Puchhammer | |
| 7,922,773 B1 | 4/2011 | Kuiken | |
| 8,016,893 B2 | 9/2011 | Weinberg et al. | |
| 8,021,435 B2 | 9/2011 | Bravo Castillo | |
| 8,052,185 B2 | 11/2011 | Madhani | |
| 8,100,986 B2 | 1/2012 | Puchhammer et al. | |
| 8,141,925 B2 | 3/2012 | Mizuno et al. | |
| 8,197,554 B2 | 6/2012 | Whiteley et al. | |
| 8,257,446 B2 | 9/2012 | Puchhammer | |
| 8,337,568 B2 | 12/2012 | Macduff | |
| 8,343,234 B2 | 1/2013 | Puchhammer | |
| 8,491,666 B2 | 7/2013 | Schulz | |
| 8,579,991 B2 | 11/2013 | Puchhammer | |
| 8,593,255 B2 | 11/2013 | Pang et al. | |
| 8,657,887 B2 | 2/2014 | Gill | |
| 8,662,552 B2 | 3/2014 | Torres-Jara | |
| 8,663,339 B2 | 3/2014 | Inschlag et al. | |
| 8,690,963 B2 | 4/2014 | Puchhammer | |
| 8,696,763 B2 | 4/2014 | Gill | |
| 8,739,315 B2 | 6/2014 | Baacke | |
| 8,747,486 B2 | 6/2014 | Kawasaki et al. | |
| 8,795,387 B1 | 8/2014 | Razink | |
| 8,803,844 B1 | 8/2014 | Green et al. | |
| 8,808,397 B2 | 8/2014 | Gow | |
| 8,828,096 B2 | 9/2014 | Gill | |
| 8,900,327 B2 | 12/2014 | Bertels et al. | |
| 8,915,528 B2 | 12/2014 | Haslinger | |
| 8,951,303 B2 | 2/2015 | Dehoff et al. | |
| 8,979,943 B2 | 3/2015 | Evans et al. | |
| 8,984,736 B2 | 3/2015 | Radocy | |
| 8,986,395 B2 | 3/2015 | McLeary | |
| 8,995,760 B2 | 3/2015 | Gill | |
| 8,999,003 B2 | 4/2015 | Wenstrand et al. | |
| 9,016,744 B2 | 4/2015 | Starkey | |
| 9,017,422 B2 | 4/2015 | Locker | |
| 9,039,057 B2 | 5/2015 | Schvalb et al. | |
| 9,071,170 B2 | 6/2015 | Baba et al. | |
| 9,072,614 B2 | 7/2015 | Starkey et al. | |
| 9,072,616 B2 | 7/2015 | Schulz | |
| 9,114,028 B2 | 8/2015 | Langenfeld et al. | |
| 9,278,012 B2 | 3/2016 | Gill | |
| 9,320,621 B2 | 4/2016 | Iversen et al. | |
| 9,333,096 B2 | 5/2016 | Perez de Alderete et al. | |
| 9,364,364 B2 | 6/2016 | Williams | |
| 9,370,430 B2 | 6/2016 | Macduff | |
| 9,375,319 B2 | 6/2016 | Macduff | |
| 9,375,325 B2 | 6/2016 | Garrec et al. | |
| 9,381,099 B2 | 7/2016 | Perry et al. | |
| 9,387,095 B2 | 7/2016 | McLeary et al. | |
| 9,402,749 B2 | 8/2016 | Gill et al. | |
| 9,435,400 B2 | 9/2016 | Cheung et al. | |
| 9,456,909 B2 | 10/2016 | Johnson et al. | |
| 9,463,085 B1 | 10/2016 | Theobald | |
| 9,463,100 B2 | 10/2016 | Gill | |
| 9,468,540 B2 | 10/2016 | Nagatsuka et al. | |
| 9,474,630 B2 | 10/2016 | Veatch | |
| 9,474,631 B2 | 10/2016 | Veatch | |
| 9,510,958 B2 | 12/2016 | Mori | |
| 9,579,218 B2 | 2/2017 | Lipsey et al. | |
| 9,579,219 B2 | 2/2017 | Amend, Jr. et al. | |
| 9,585,771 B2 | 3/2017 | Baba et al. | |
| 9,592,134 B2 | 3/2017 | Varley | |
| 9,629,731 B2 | 4/2017 | Thompson, Jr. et al. | |
| 9,636,270 B2 | 5/2017 | Miyazawa | |
| 9,707,103 B2 | 7/2017 | Thompson, Jr. et al. | |
| 9,720,515 B2 | 8/2017 | Wagner et al. | |
| 9,730,813 B2 | 8/2017 | Evans et al. | |
| 9,737,418 B2 | 8/2017 | Veatch | |
| 9,744,055 B2 | 8/2017 | Engeberg et al. | |
| 9,814,604 B2 | 11/2017 | Jury | |

(56) References Cited

U.S. PATENT DOCUMENTS

| | | |
|---|---|---|
| 9,839,534 B2 | 12/2017 | Lipsey et al. |
| 9,861,499 B2 | 1/2018 | Sensinger |
| 9,877,848 B2 | 1/2018 | Ikebe |
| 9,889,059 B2 | 2/2018 | Arakawa |
| 9,913,737 B2 | 3/2018 | Hunter |
| 9,931,229 B2 | 4/2018 | Veatch |
| 9,974,667 B1 | 5/2018 | Cazenave |
| 9,999,522 B2 | 6/2018 | Gill |
| 10,004,611 B2 | 6/2018 | Iversen et al. |
| 10,004,612 B2 | 6/2018 | Iversen et al. |
| 10,022,248 B2 | 7/2018 | Thompson, Jr. et al. |
| 10,028,880 B2 | 7/2018 | Arata et al. |
| 10,034,780 B2 | 7/2018 | Lipsey et al. |
| 10,045,865 B2 | 8/2018 | Veatch |
| 10,045,866 B2 | 8/2018 | Armbruster |
| 10,052,216 B2 | 8/2018 | Moyer et al. |
| 10,076,425 B2 | 9/2018 | Farina et al. |
| 10,092,423 B2 | 10/2018 | Goldfarb et al. |
| 10,265,197 B2 | 4/2019 | Gill et al. |
| 10,318,863 B2 | 8/2019 | Lock et al. |
| 10,369,016 B2 | 8/2019 | Lipsey et al. |
| 10,369,024 B2 | 8/2019 | Gill |
| 10,398,576 B2 | 9/2019 | Gill et al. |
| 10,449,063 B2 | 10/2019 | Gill |
| 10,610,385 B2 | 4/2020 | Meijer et al. |
| 10,973,660 B2 | 4/2021 | Gill et al. |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2003/0090115 A1 | 5/2003 | Kim et al. |
| 2004/0002672 A1 | 1/2004 | Carlson |
| 2004/0054423 A1 | 3/2004 | Martin |
| 2004/0078299 A1 | 4/2004 | Down-Logan et al. |
| 2004/0103740 A1 | 6/2004 | Townsend et al. |
| 2004/0181289 A1 | 9/2004 | Bedard et al. |
| 2004/0182125 A1 | 9/2004 | McLean |
| 2005/0021154 A1 | 1/2005 | Brimalm |
| 2005/0021155 A1 | 1/2005 | Brimalm |
| 2005/0093997 A1 | 5/2005 | Dalton et al. |
| 2005/0101693 A1 | 5/2005 | Arbogast et al. |
| 2005/0102037 A1 | 5/2005 | Matsuda |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0032884 A1 | 2/2007 | Veatch |
| 2007/0058860 A1 | 3/2007 | Harville et al. |
| 2007/0061111 A1 | 3/2007 | Jung et al. |
| 2007/0071314 A1 | 3/2007 | Bhatti et al. |
| 2007/0102228 A1 | 5/2007 | Shiina et al. |
| 2007/0137351 A1 | 6/2007 | Schwendemann |
| 2007/0230832 A1 | 10/2007 | Usui et al. |
| 2007/0260328 A1 | 11/2007 | Bertels et al. |
| 2007/0276303 A1 | 11/2007 | Jenner, Jr. |
| 2008/0058668 A1 | 3/2008 | Seyed Momen et al. |
| 2008/0097269 A1 | 4/2008 | Weinberg et al. |
| 2008/0146981 A1 | 6/2008 | Greenwald et al. |
| 2008/0215162 A1 | 9/2008 | Farnsworth et al. |
| 2008/0260218 A1 | 10/2008 | Smith et al. |
| 2008/0262634 A1 | 10/2008 | Puchhammer |
| 2009/0145254 A1 | 6/2009 | Hirabayashi et al. |
| 2009/0213379 A1 | 8/2009 | Carroll et al. |
| 2010/0016990 A1 | 1/2010 | Kurtz |
| 2010/0036507 A1 | 2/2010 | Gow |
| 2010/0116078 A1 | 5/2010 | Kim |
| 2010/0274365 A1 | 10/2010 | Evans et al. |
| 2011/0048098 A1 | 3/2011 | Rollins et al. |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |
| 2012/0004884 A1 | 1/2012 | Fillol et al. |
| 2012/0014571 A1 | 1/2012 | Wong et al. |
| 2012/0061155 A1 | 3/2012 | Berger et al. |
| 2012/0099788 A1 | 4/2012 | Bhatti et al. |
| 2012/0123558 A1 | 5/2012 | Gill |
| 2012/0204665 A1 | 8/2012 | Baudasse |
| 2012/0221122 A1* | 8/2012 | Gill .......... A61F 2/70 |
| | | 623/64 |
| 2012/0229828 A1 | 9/2012 | Gill |
| 2012/0280812 A1 | 11/2012 | Sheikman et al. |
| 2012/0286629 A1 | 11/2012 | Johnson et al. |
| 2012/0303136 A1 | 11/2012 | Macduff |
| 2012/0330432 A1 | 12/2012 | Fong |
| 2012/0330439 A1 | 12/2012 | Goldfarb et al. |
| 2013/0030550 A1* | 1/2013 | Jopek .......... A61F 2/588 |
| | | 623/64 |
| 2013/0053984 A1 | 2/2013 | Hunter et al. |
| 2013/0076699 A1 | 3/2013 | Spencer |
| 2013/0144197 A1 | 6/2013 | Ingimundarson et al. |
| 2013/0175816 A1 | 7/2013 | Kawasaki et al. |
| 2013/0226315 A1 | 8/2013 | Varley |
| 2013/0253705 A1 | 9/2013 | Goldfarb et al. |
| 2013/0268090 A1 | 10/2013 | Goldfarb et al. |
| 2013/0268094 A1 | 10/2013 | Van Wiemeersch |
| 2013/0310949 A1 | 11/2013 | Goldfarb et al. |
| 2014/0060236 A1 | 3/2014 | Watanabe |
| 2014/0148918 A1 | 5/2014 | Pedersen et al. |
| 2014/0148919 A1 | 5/2014 | Pedersen et al. |
| 2014/0236314 A1 | 8/2014 | Van Wiemeersch |
| 2014/0251056 A1 | 9/2014 | Preuss |
| 2014/0277588 A1 | 9/2014 | Patt et al. |
| 2014/0288665 A1* | 9/2014 | Gill .......... A61H 1/0288 |
| | | 623/24 |
| 2014/0288666 A1 | 9/2014 | Gill et al. |
| 2014/0324189 A1 | 10/2014 | Gill et al. |
| 2014/0371871 A1 | 12/2014 | Farina et al. |
| 2015/0112448 A1 | 4/2015 | Scott et al. |
| 2015/0142082 A1 | 5/2015 | Simon et al. |
| 2015/0183069 A1 | 7/2015 | Lee |
| 2015/0190245 A1 | 7/2015 | McLeary et al. |
| 2015/0216679 A1 | 8/2015 | Lipsey et al. |
| 2015/0216681 A1 | 8/2015 | Lipsey et al. |
| 2015/0351935 A1 | 12/2015 | Donati et al. |
| 2015/0360369 A1 | 12/2015 | Ishikawa et al. |
| 2015/0374515 A1 | 12/2015 | Meijer et al. |
| 2016/0089251 A1 | 3/2016 | Mandl et al. |
| 2016/0166409 A1 | 6/2016 | Goldfarb et al. |
| 2016/0250044 A1 | 9/2016 | Iversen et al. |
| 2016/0287422 A1 | 10/2016 | Kelly et al. |
| 2016/0296345 A1 | 10/2016 | Deshpande et al. |
| 2016/0367383 A1 | 12/2016 | Sensinger et al. |
| 2017/0007424 A1 | 1/2017 | Gill |
| 2017/0014245 A9 | 1/2017 | Hunter |
| 2017/0049586 A1 | 2/2017 | Gill et al. |
| 2017/0168565 A1 | 6/2017 | Cohen et al. |
| 2017/0340459 A1 | 11/2017 | Mandelbaum |
| 2018/0036145 A1 | 2/2018 | Jury et al. |
| 2018/0064563 A1* | 3/2018 | Gill .......... A61F 2/586 |
| 2018/0071115 A1 | 3/2018 | Lipsey et al. |
| 2018/0098862 A1 | 4/2018 | Kuiken et al. |
| 2018/0116829 A1 | 5/2018 | Gaston et al. |
| 2018/0133032 A1 | 5/2018 | Poirters |
| 2018/0140441 A1 | 5/2018 | Poirters |
| 2018/0168830 A1 | 6/2018 | Evans et al. |
| 2018/0202538 A1* | 7/2018 | Wilson-Jones .......... F16H 55/24 |
| 2018/0207005 A1 | 7/2018 | Chen et al. |
| 2018/0221177 A1 | 8/2018 | Kaltenbach et al. |
| 2018/0256365 A1 | 9/2018 | Bai |
| 2018/0256366 A1 | 9/2018 | Bai |
| 2018/0256367 A1* | 9/2018 | Bai .......... A61F 2/54 |
| 2018/0263791 A1 | 9/2018 | Bai |
| 2018/0296368 A1 | 10/2018 | Gill |
| 2018/0303633 A1 | 10/2018 | Yi |
| 2019/0091040 A1 | 3/2019 | Gill |
| 2019/0183661 A1 | 6/2019 | Gill |
| 2019/0209345 A1 | 7/2019 | LaChappelle |

(56) References Cited

U.S. PATENT DOCUMENTS

| | | | |
|---|---|---|---|
| 2019/0216618 A1 | 7/2019 | Gill | |
| 2019/0343660 A1 | 11/2019 | Gill | |
| 2019/0368237 A1* | 12/2019 | Distefano | E05B 79/12 |
| 2019/0380846 A1 | 12/2019 | Lipsey et al. | |
| 2020/0047351 A1 | 2/2020 | Zappatore | |
| 2020/0054466 A1 | 2/2020 | Gill et al. | |
| 2020/0197193 A1 | 6/2020 | Byrne et al. | |
| 2020/0268532 A1 | 8/2020 | Meijer et al. | |
| 2020/0306059 A1* | 10/2020 | Cornman | B25J 9/126 |
| 2021/0145610 A1* | 5/2021 | Rivera | A61F 2/70 |
| 2021/0307934 A1 | 10/2021 | Gill et al. | |
| 2021/0361446 A1* | 11/2021 | Griebling | A61F 2/586 |
| 2022/0160521 A1 | 5/2022 | Benning | |
| 2022/0339009 A1 | 10/2022 | Benning | |
| 2023/0088565 A1 | 3/2023 | Benning | |

FOREIGN PATENT DOCUMENTS

| | | |
|---|---|---|
| CN | 103830025 | 8/2015 |
| CN | 103705323 | 3/2016 |
| CN | 106994694 | 8/2017 |
| CN | 106491250 | 9/2018 |
| DE | 309 367 | 11/1918 |
| DE | 319 092 | 2/1920 |
| DE | 323 970 | 8/1920 |
| DE | 24 34 834 | 2/1976 |
| DE | 26 07 499 | 9/1977 |
| DE | 198 54 762 | 6/2000 |
| DE | 101 05 814 | 9/2002 |
| DE | 203 15 575 | 1/2004 |
| DE | 698 16 848 | 4/2004 |
| DE | 10 2012 009 699 | 11/2013 |
| DE | 10 2017 005 761 | 2/2020 |
| DE | 10 2017 005 762 | 2/2020 |
| DE | 10 2017 005 764 | 2/2020 |
| DE | 10 2017 005 765 | 2/2020 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 617 103 | 1/2006 |
| EP | 1 557 547 | 1/2011 |
| EP | 2 532 927 | 12/2012 |
| EP | 2 612 619 | 7/2013 |
| EP | 2 616 017 | 7/2013 |
| EP | 2 653 137 | 10/2013 |
| EP | 2 664 302 | 11/2013 |
| EP | 2 719 361 | 4/2014 |
| EP | 2 114 315 | 5/2016 |
| EP | 2 890 333 | 12/2016 |
| EP | 2 978 389 | 5/2017 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 357 725 A | 7/2001 |
| GB | D 3023680 | 4/2006 |
| GB | 2 444 679 | 6/2008 |
| JP | 53-011456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| JP | 2018-167375 | 11/2018 |
| WO | WO 95/024875 | 9/1995 |
| WO | WO 96/023643 | 8/1996 |
| WO | WO 99/021517 | 5/1999 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044052 | 4/2008 |
| WO | WO 2008/044207 | 4/2008 |
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2013/038143 | 3/2013 |
| WO | WO 2014/016581 | 1/2014 |
| WO | WO 2014/027897 | 2/2014 |
| WO | WO 2015/120076 | 8/2015 |
| WO | WO 2015/120083 | 8/2015 |
| WO | WO 2015/128604 | 9/2015 |
| WO | WO 2017/061879 | 4/2017 |
| WO | WO 2017/084637 | 5/2017 |
| WO | WO 2017/199127 | 11/2017 |
| WO | WO 2017/212128 | 12/2017 |
| WO | WO 2018/006722 | 1/2018 |
| WO | WO 2018/054945 | 3/2018 |
| WO | WO 2018/056799 | 3/2018 |
| WO | WO 2018/096188 | 5/2018 |
| WO | WO 2018/121983 | 7/2018 |
| WO | WO 2018/130428 | 7/2018 |
| WO | WO 2018/132711 | 7/2018 |
| WO | WO 2018/158554 | 9/2018 |
| WO | WO 2018/178420 | 10/2018 |
| WO | WO 2018/180782 | 10/2018 |
| WO | WO 2018/218129 | 11/2018 |
| WO | WO 2020/208557 | 10/2020 |
| WO | WO 2020/234777 | 11/2020 |
| WO | WO 2021/053557 | 3/2021 |
| WO | WO 2021/095014 | 5/2021 |

OTHER PUBLICATIONS

Albu-Schaffer et al., "Soft Robotics", IEEE Robotics & Automation Magazine, Sep. 2008, vol. 15, No. 3, pp. 20-30.

Antonio et al., "A Virtual Upper Limb Prosthesis as a Training System", 7th International Conference on Electrical Engineering, Computing Science and Automatic Control (CCE 2010) Tuxtla Gutiérrez, Chiapas, Mexico. Sep. 8-10, 2010, pp. 210-215.

Bellman et al., "SPARKy 3: Design of an Active Robotic Ankle Prosthesis with Two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale, AZ, pp. 511-516.

(56) References Cited

OTHER PUBLICATIONS

Belter et al., "Mechanical Design and Performance Specifications of Anthropomorphic Prosthetic Hands: A Review", JRRD, Jan. 2013, vol. 50, No. 5, pp. 599-617.

Biddiss et al., "Consumer Design Priorities for Upper Limb Prosthetics", Disability and Rehabilitation: Assistive Technology, Nov. 2007, vol. 2, No. 6, pp. 346-357.

Biddiss et al., "Upper Limb Prosthesis Use and Abandonment: A Survey of the Last 25 Years", Prosthetics and Orthotics International, Sep. 2007, vol. 31, No. 3, pp. 236-257.

Biddiss et al., "Upper-Limb Prosthetics: Critical Factors in Device Abandonment", American Journal of Physical Medicine & Rehabilitation, Dec. 2007, vol. 86, No. 12, pp. 977-987.

Chicoine et al., "Prosthesis-Guided Training of Pattern Recognition-Controlled Myoelectric Prosthesis", in Proceedings of the 34th Annual International Conference of the IEEE EMBSs, San Diego, CA, Aug. 28-Sep. 1, 2012, pp. 1876-1879.

Childress et al., "Control of Limb Prostheses", American Academy of Orthopaedic Surgeons, Mar. 2004, Chapter 12, pp. 173-195.

Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.

Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.

Connolly, "Prosthetic Hands from Touch Bionics", Industrial Robot, Emerald Group Publishing Limited, Jun. 2008, vol. 35, No. 4, pp. 290-293.

Controzzi et al., "Miniaturized Non-Back-Drivable Mechanism for Robotic Applications", Mechanism and Machine Theory, Oct. 2010, vol. 45, No. 10, pp. 1395-1406.

Cotton et al., "Control Strategies for A Multiple Degree Of Freedom Prosthetic Hand", Measurement + Control, Feb. 2007, vol. 40, No. 1, pp. 24-27.

Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.

"DC Circuit Theory", https://www.electronics-tutorials.ws/dccircuits/dcp_1.html, Date verified by the Wayback Machine Apr. 23, 2013, pp. 16.

Dechev et al., "Multiple Finger, Passive Adaptive Grasp Prosthetic Hand", Mechanism and Machine Theory, Oct. 1, 2001, vol. 36, No. 10, pp. 1157-1173.

Dellorto, Danielle, "Bionic Hands Controlled by iPhone App", CNN, Apr. 12, 2013, pp. 4 http://www.cnn.com/2013/04/12/health/bionic-hands.

"DuPont Engineering Design—The Review of DuPont Engineering Polymers in Action", http://www.engpolymer.co.kr/x_data/magazine/engdesign07_2e.pdf, Feb. 2007, pp. 16.

Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.

Fougner et al., "Control of Upper Limb Prostheses: Terminology and Proportional Myoelectric Control—A Review", IEEE Transactions on Neural Systems Rehabilitation Engineering, Sep. 2012, vol. 20, No. 5, pp. 663-677.

Fukuda et al., "Training of Grasping Motion Using a Virtual Prosthetic Control System", 2010 IEEE International Conference on Systems Man and Cybernetics (SMC), Oct. 10-13, 2010, pp. 1793-1798.

Gaine et al., "Upper Limb Traumatic Amputees. Review of Prosthetic Use", The Journal of Hand Surgery, Feb. 1997, vol. 22B, No. 1, pp. 73-76.

Grip Chips™, Datasheet, May 15, 2014, Issue 1, http://touchbionics.com/sites/default/files/files/Grip%20Chip%20datasheet%20May%202014.pdf, pp. 1.

Heckathorne, Craig W., "Components for Electric-Powered Systems", American Academy of Orthopaedic Surgeons, Mar. 2004, Chapter 11, pp. 145-171.

Hojjat et al., "A Comprehensive Study on Capabilities and Limitations of Roller-Screw with Emphasis on Slip Tendency", Mechanism and Machine Theory, Oct. 2009, vol. 44, No. 10, pp. 1887-1899.

Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-091008-11.

Jebsen et al., "An Objective and Standardized Test of Hand Function", Archives of Physical Medicine and Rehabilitation, Jun. 1969, vol. 50, No. 6, pp. 311-319.

Johannes et al., "An Overview of the Developmental Process for the Modular Prosthetic Limb," John Hopkins APL Technical Digest, 2011, vol. 30, No. 3, pp. 207-216.

Kent et al., "Electromyogram Synergy Control of a Dexterous Artificial Hand to Unscrew and Screw Objects", Journal of Neuroengineering and Rehabilitation, Mar. 2014, vol. 11, No. 1, pp. 1-20.

Kermani et al., "Friction Identification and Compensation in Robotic Manipulators", IEEE Transactions on Instrumentation and Measurement, Dec. 2007, vol. 56, No. 6, pp. 2346-2353.

Kuiken et al., "Targeted Muscle Reinnervation for Real-Time Myoelectric Control of Multifunction Artificial Arms", JAMA, Feb. 11, 2009, vol. 301, No. 6, pp. 619-628.

Kyberd et al., "Two-Degree-of-Freedom Powered Prosthetic Wrist", Journal of Rehabilitation Research & Development, Jul. 2011, vol. 48, No. 6, pp. 609-617.

Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.

Light et al., "Development of a Lightweight and Adaptable Multiple-Axis Hand Prosthesis", Medical Engineering & Physics 22, 2000, pp. 679-684.

Light et al., "Establishing a Standardized Clinical Assessment Tool of Pathologic and Prosthetic Hand Function: Normative Data, Reliability, and Validity", Archives of Physical Medicine and Rehabilitation, Jun. 2002, vol. 83, pp. 776-783.

Mace et al., "Augmenting Neuroprosthetic Hand Control Through Evaluation of a Bioacoustic Interface", IEEE/RSJ International Conference on Intelligent Robots and Systems (IROS), Tokyo, Japan, Nov. 3-7, 2013, pp. 7.

Majd et al., "A Continuous Friction Model for Servo Systems with Stiction", in Proceedings of the IEEE Conference on Control Applications, Sep. 28-29, 1995, pp. 296-301.

Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.

Maxon Precision Motors, Inc., "Maxon Flat Motor: EX 10 flat 10 mm, brushless, 0.25 Watt", Specification, May 2011, p. 181.

Maxon Precision Motors, Inc., "Maxon EC Motor: EC10 10 mm, brushless, 8 Watt", Specification, May 2011, p. 140.

Miller et al., "Summary and Recommendations of the Academy's State of the Science Conference on Upper Limb Prosthetic Outcome Measures", Journal of Prosthetics Orthotics, Oct. 2009, vol. 21, pp. 83-89.

Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.

Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.

Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.

Osborn et al., "Utilizing Tactile Feedback for Biomimetic Grasping Control in Upper Limb Prostheses", Department of Biomedical Engineering, Johns Hopkins University, Baltimore, USA, Nov. 5, 2013, pp. 4.

(56) References Cited

OTHER PUBLICATIONS

Pedrocchi et al., "MUNDUS Project: Multimodal Neuroprosthesis for Daily Upper Limb Support", Journal of Neuroengineering and Rehabilitation, Jul. 2013, vol. 10, No. 66, pp. 20.

Pinzur et al., "Functional Outcome Following Traumatic Upper Limb Amputation and Prosthetic Limb Fitting", The Journal of Hand Surgery, Sep. 1994. vol. 19, pp. 836-839.

Press Release, "Touch Bionics Introduce Digitally Controlled Supro Wrist". http://www.touchbionics.com/news-events/news/touch-bionics-introduce-digitally-controlled-supro-wrist, May 3, 2016 in 2 pages.

Raspopovic et al., "Restoring Natural Sensory Feedback in Real-Time Bidirectional Hand Prostheses", Science Translational Medicine, Feb. 5, 2014, vol. 6, No. 222, pp. 1-10.

Resnik et al., "The DEKA Arm: Its Features, Functionality, and Evolution During the Veterans Affairs Study to Optimize the DEKA Arm", Prosthetics and Orthotics International, Oct. 2013, vol. 38, No. 6, pp. 492-504.

Scheme et al., "Electromyogram Pattern Recognition for Control of Powered Upper-Limb Prostheses: State of the Art and Challenges for Clinical Use", Journal of Rehabilitation Research & Development (JRRD), Jul. 2011, vol. 48, No. 6, pp. 643-659.

Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.

Sensinger et al., "Cycloid vs. Harmonic Drives for use in High Ratio, Single Stage Robotic Transmissions", 2012 IEEE Conference on Robotics and Automation (ICRA), Saint Paul, MN, USA, May 14-18, 2012, pp. 4130-4135.

Sensinger, "Efficiency of High-Sensitivity Gear Trains, such as Cycloid Drives", Journal of Mechanical Design, Jul. 2013, vol. 135, No. 7, pp. 071006-1-071006-9.

Sensinger et al., "Exterior vs. Interior Rotors in Robotic Brushless Motors", 2011 IEEE International Conference on Robotics and Automation (ICRA), Shanghai, China, May 9-13, 2011, pp. 2764-2770.

Sensinger, "Selecting Motors for Robots Using Biomimetic Trajectories: Optimum Benchmarks, Windings, and other Considerations," 2010 IEEE International Conference on Robotics and Automation (ICRA), Anchorage, AL, USA, May 3-8, 2010, pp. 4175-4181.

Sensinger, "Unified Approach to Cycloid Drive Profile, Stress, and Efficiency Optimization", Journal of Mechanical Design, Feb. 2010, vol. 132, pp. 024503-1-024503-5.

Sensinger et al., "User-Modulated Impedance Control of a Prosthetic Elbow in Unconstrained, Perturbed Motion", IEEE Transactions on Biomedical Engineering, Mar. 2008, vol. 55, No. 3, pp. 1043-1055.

Stix, Gary, "Phantom Touch: Imbuing a Prosthesis with Manual Dexterity", Scientific American, Oct. 1998, pp. 41 & 44.

"Supro Wrist", Touch Bionics, https://web.archive.org/web/20160928141440/http://www.touchbionics.com/products/supro-wrist as archived Sep. 28, 2016 in 3 pages.

Sutton et al., "Towards a Universal Coupler Design for Modern Powered Prostheses", MEC 11 Raising the Standard, Proceedings of the 2011 MyoElectric Controls/Powered Prosthetics Symposium Fredericton, New Brunswick, Canada, Aug. 14-19, 2011, pp. 5.

Tan et al., "A Neural Interface Provides Long-Term Stable Natural Touch Perception", Science Translational Medicine, Oct. 8, 2014, vol. 6, No. 257, pp. 1-11.

Tang, "General Concepts of Wrist Biomechanics and a View from Other Species", The Journal of Hand Surgery, European Volume Aug. 2008, vol. 33, No. 4, pp. 519-525.

Toledo et al., "A Comparison of Direct and Pattern Recognition Control for a Two Degree-of-Freedom Above Elbow Virtual Prosthesis", in Proceedings 34th Annual International Conference of the IEEE EMBS, Aug. 2012, pp. 4332-4335.

"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.

Touch Bionics PowerPoint Presentation in 3 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).

Touch Bionics PowerPoint Slide in 1 page, believed to be presented at Advanced Arm Dynamics company Jan. 11, 2016. (Applicant requests that the Examiner consider this reference as qualifying as prior art as of the date indicated, but Applicant does not admit its status as prior art by submitting it here and reserves the right to challenge the reference's prior art status at a later date).

Touch Bionics Screenshots of video in PowerPoint Presentation in 4 pages, believed to be shown at ISPO Conference in Leipzig, Germany, May 2016. (Applicant requests that the Examiner consider this reference as qualifying as prior art as of the date indicated, but Applicant does not admit its status as prior art by submitting it here and reserves the right to challenge the reference's prior art status at a later date).

Townsend, William T., "Description of a Dexterous Robotic Grasper", Journal of the Robotics Society of Japan, Sep. 2000, vol. 18, No. 6, pp. 798-801.

Trachtenberg et al., "Radio Frequency Identification, An Innovative Solution to Guide Dexterous Prosthetic Hands", 33rd Annual International Conference of the IEEE EMBS, Boston, MA, Aug. 30-Sep. 3, 2011, pp. 4.

Vilarino, Martin, "A Novel Wireless Controller for Switching among Modes for an Upper-Limb Prosthesis", The Academy TODAY, Jan. 2014, vol. 10, No. 1, pp. A-12 to A-15.

Weir et al., "Design of Artificial Arms and Hands for Prosthetic Applications", Biomedical Engineering and Design Handbook, Jul. 2009, vol. 2, pp. 537-598.

Weir et al., "The Design and Development of a Synergetic Partial Hand Prosthesis with Powered Fingers", RESNA '89, Proceedings of the 12th Annual Conference, Technology for the Next Decade, Jun. 25-30, 1989, pp. 473-474.

Wettels et al., "Grip Control Using Biomimetic Tactile Sensing Systems", IEEE/ASME Transactions on Mechatronics, Dec. 2009, vol. 14, No. 6, pp. 718-723.

Whiteside et al., "Practice Analysis Task Force: Practice Analysis of the Disciplines of Orthotics and Prosthetics", American Board for Certification in Orthotics and Prosthetics, Inc., 2000, pp. 1-51.

Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.

Zampagni et al., "A Protocol for Clinical Evaluation of the Carrying Angle of the Elbow by Anatomic Landmarks", Journal of Shoulder and Elbow Surgery, Jan. 1, 2008, vol. 17, No. 1, pp. 106-112.

9 Worm Gear Pair, KHK Technical Information, Oct. 21, 2008, pp. 291-299.

Baek et al., "Design and Control of a Robotic Finger for Prosthetic Hands", Proceedings of the 1999 IEEE International Conference on Intelligent Robots and Systems, pp. 113-117.

Bretthauer et al., "A New Adaptive Hand Prosthesis", Handchirurgie Mikrochirurgie Plastische Chirurgie, Feb. 2008, pp. 40-45.

Butterfaß et al., "DLR-Hand II: Next Generation of a Dextrous Robot Hand", IEEE International Conference on Robotics and Automation, Seoul, Korea, May 21-26, 2001, vol. 1, pp. 109-114.

Edsinger-Gonzales, Aaron, "Design of a Compliant and Force Sensing Hand for a Humanoid Robot", 2005, pp. 5.

AMA, Excerpts from American Medical Association, Guides to the Evaluation of Permanent Impairment (5th ed. 2000), pp. 432-453.

Fildes, Jonathan, "Bionic Hand Wins Top Tech Prize", BBC News, Jun. 9, 2008, http://news.bbc.co.uk/2/hi/science/nature/7443866.stm, pp. 3.

Gaiser et al., "A New Anthropomorphic Robotic Hand", 2008 8th IEEE-RAS International Conference on Humanoid Robots, Dec. 1-3, 2008, Daejeon, Korea, pp. 418-422.

(56) References Cited

OTHER PUBLICATIONS

"iLimb Bionic Hand Now Ready for Market", Technovelgy.com, www.technovelgy.com/ct/Science-Fiction-News.asp?NewsNum=1125, as printed Jul. 6, 2020 in 3 pages.
Kargov et al., "Applications of a Fluidic Artificial Hand in the Field of Rehabilitation", Rehabilitation Robotics, Ch. 15, Aug. 2007, pp. 261-286.
Kargov et al., "Development of a Multifunctional Cosmetic Prosthetic Hand", Proceedings for the 2007 IEEE 10th International Conference on Rehabilitation Robotics, Jun. 12-15, 2007, Noordwijk, The Netherlands, pp. 550-553.
Kargov et al., "Modularly Designed Lightweight Anthropomorphic Robot Hand", 2006 IEEE International Conference on Multisensor Fusion and Integration for Intelligent Systems, Sep. 3-6, 2006, Heidelberg, Germany, pp. 155-159.
Kawasaki et al., "Design and Control of Five-Fingered Haptic Interface Opposite to Human Hand", IEEE Transactions on Robotics, Oct. 2007, vol. 23, No. 5., pp. 909-918.
Lotti et al., "UBH 3: A Biologically Inspired Robotic Hand", Jan. 2004, pp. 7.
MEC '05: Integrating Prosthetics and Medicine, University of New Brunswick's MyoElectric Controls/Powered Prosthetics Symposium, Aug. 17-19, 2005, Fredericton NB Canada, pp. 260.
"Motor Technology—Girard Gearboxes Low Backlash Principle Explained", Motor Technology, https://www.motec.co.uk/tip-gearbox_principle.htm as printed May 23, 2012 in 3 pages.
Poppe, Zytel HTN Provides a Helping Hand, DuPont Engineering Design 8 (2007), pp. 3.
Puig et al., "A Methodology for the Design of Robotic Hands with Multiple Fingers", International Journal of Advanced Robotic Systems, 2008, vol. 5, No. 2, pp. 177-184.
Ryew et al., "Robotic Finger Mechanism with New Anthropomorphic Metacarpal Joint", 26th Annual Conference of the IEEE Industrial Electronics Society, 2000. IECON 2000, vol. 1, pp. 416-421.
Schulz et al., "Die Entwicklung Einer Multifunktionalen Kosmetischen Handprothese", Prothetik, Orthopädie-Technik Aug. 2006, pp. 627-632.
The Weir Thesis ("Weir Thesis") is entitled "An Externally-Powered, Myo-Electrically Controlled Synergetic Prosthetic Hand for the Partial-Hand Amputee", published Aug. 1989, pp. 365.
Ward, Derek Kempton, "Design of a Two Degree of Freedom Robotic Finger", Sep. 1996, pp. 155.
Weir et al., "A Myoelectrically Controlled Prosthetic Hand for Transmetacarpal Amputations", JPO Journal of Prosthetics and Orthotics, Jun. 2001, vol. 13, No. 2, pp. 26-31.
"World's First Bionic Hand Factory Opened by Scottish Company", DailyMail.com, Jan. 8, 2008, https://www.dailymail.co.uk/sciencetech/article-506661/Worlds-bionic-hand-factory-opened-Scottish-company.html, pp. 4.
Adee, Sally, "A 'Manhattan Project' for the Next Generation of Bionic Arms", IEEE Spectrum, https://spectrum.ieee.org/a-manhattan-project-for-the-next-generation-of-bionic-arms#toggle-gdpr, Mar. 22, 2008, pp. 3.
Dimery, Rob, "1993: First Bionic Arm", Guinness World Records, https://www.guinnessworldrecords.com/news/60at60/2015/8/1993-first-bionic-arm-392887, Aug. 18, 2015, pp. 2.
"EMAS: The First Bionic Arm", National Museums Scotland, https://web.archive.org/web/20200805045443/https://www.nms.ac.uk/explore-our-collections/stories/science-and-technology/made-in-scotland-changing-the-world/scottish-science-innovations/emas-bionic-arm/, archived Aug. 5, 2020, pp. 8.
Goggins, Sophie, "EMAS—An Award Winning Bionic Arm", National Museums Scotland, https://blog.nms.ac.uk/2017/11/29/emas-an-award-winning-bionic-arm/, Nov. 29, 2017, pp. 6.
Gow, David, "The Development of the Edinburgh Modular Arm System", Institute of Biomedical Engineering, University of New Brunswick, MEC '99 "Narrowing the Gap", pp. 64-66.
Grant, C. "Touch Bionics has i-LIMB Bionic Arm to go with your Bionic Hand", Engadget, https://www.engadget.com/2008-01-05-touch-bionics-has-i-limb-bionic-arm-to-go-with-your-bionic-hand.html, Jan. 6, 2008, p. 1.
Greenemeier, Larry, "Bionic Hand Recognized as Top Invention", Scientific American, https://blogs.scientificamerican.com/news-blog/bionic-hand-recognized-as-top-inven-2008-11-06, Nov. 6, 2008, pp. 3.
"i-Limb™ Hand", Touch Bionics, User Manual, Revision 1.5, 2007, pp. 12.
International Search Report and Written Opinion in Application No. PCT/IB2020/060724, dated Mar. 31, 2021.
"Living with a Dead Man's Hand", BBC News, http://news.bbc.co.uk/2/hi/health/980069.stm, Oct. 22, 2000, pp. 4.
Miller et al., "Control of a Six Degree of Freedom Prosthetic Arm After Targeted Muscle Reinnervation Surgery", Archives of Physical Medicine and Rehabilitation, Nov. 2008, vol. 89, pp. 2057-2065.
Pilgrim, Michael, "Meet the Man Who Was Given Britain's First Bionic Hand on the NHS—and is now Learning to Fly", Daily Mail, https://www.dailymail.co.uk/health/article-1038857/Meet-man-given-Britains-bionic-hand-NHS--learning-fly.html, Jul. 26, 2008, pp. 7.
"ProDigits The Partial Hand Solution", Touch Bionics, Next Generation Bionic Technology: Transforming the everyday lives of extraordinary people, 2007, pp. 4.
Roberts, Lizzie, "Bionic Hand Among Top Inventions of 2008", The Telegraph, https://www.telegraph.co.uk/news/health/3391089/Bionic-hand-among-top-inventions-of-2008.html, Nov. 6, 2008, pp. 2.
Shigley's Mechanical Engineering Design Eighth Edition, ISBN 0-390-76487-6 (2008), pp. 1059.
Shigley's Mechanical Engineering Design Seventh Edition, ISBN 0-07-252036-1 (2004), pp. 1064.
"The i-LIMB Hand", Touch Bionics, Fitting Guide, 2005, pp. 22.
"The i-LIMB Hand", Touch Bionics, Next Generation Bionic Technology: Transforming the everyday lives of extraordinary people, 2007, pp. 8.
Topolsky, J., "Touch Bionics i-LIMB Bionic Hand", Engadget, https://www.engadget.com/2007-07-17-touch-bionics-i-limb-bionic-hand.html, Jul. 17, 2007, p. 1.
Touch Bionics PowerPoint presentation in 32 pages, 2005, The i-LIMB™ System. (Applicant requests that the Examiner consider this reference as qualifying as prior art as of the date indicated, but Applicant does not admit its status as prior art by submitting it here and reserves the right to challenge the reference's prior art status at a later date).
Touch Bionics PowerPoint presentation in 12 pages, Oct. 17, 2006, The i-LIMB™ System. (Applicant requests that the Examiner consider this reference as qualifying as prior art as of the date indicated, but Applicant does not admit its status as prior art by submitting it here and reserves the right to challenge the reference's prior art status at a later date).
"World's First Bionic Arm for Scot", BBC News, http://news.bbc.co.uk/2/hi/health/154545.stm, Aug. 25, 1998, pp. 3.
Complaint in 36 pages and English translation in 35 pages of the Complaint filed at the Regional Court Mannheim by the law firm Bardehle Pagenberg on behalf of Vincent Systems GmbH, dated Nov. 24, 2016, in the lawsuit of *Vincent Systems GmbH* v. *Touch Bionics Limited and Touch Bionics GmbH* (collectively "Touch"), and accompanying Exhibits K1-K23 (each listed separately herewith). The Complaint and the accompanying Exhibits include information regarding Touch's products that were on sale prior to the Nov. 15, 2019 priority date of the present application and were accused of infringement. Applicant requests that the Examiner consider the information describing details of Touch's products to have been described in a printed publication, or in public use, on sale, or otherwise available to the public, prior to the Nov. 15, 2019 priority date of the present application.
Amended Complaint for Patent Infringement in 166 pages filed by Vincent Systems GmbH, dated Apr. 15, 2020, in the lawsuit of *Vincent Systems GmbH* v. *Össur hf. and Össur Americas, Inc.* (collectively "Össur"), in the United States District Court, Central District of California, Case No. 8:19-VC-02157 JLS (DFMx), including Exhibits A-J. The Amended Complaint and the accompanying Exhibits include information regarding Össur's products

(56) References Cited

OTHER PUBLICATIONS that were on sale prior to the Nov. 15, 2019 priority date of the present application and were accused of infringement. Applicant requests that the Examiner consider the information describing details of Össur's products to have been described in a printed publication, or in public use, on sale, or otherwise available to the public, prior to the Nov. 15, 2019 priority date of the present application.

Plaintiff Vincent Systems GmbH's Supplemental Disclosure of Asserted Claims and Infringement Contentions dated Jul. 16, 2020, in 38 pages, in the lawsuit of *Vincent Systems GmbH* v. *Össur hf. and Össur Americas, Inc.* (collectively "Össur"), in the United States District Court, Central District of California, Case No. 8:19-VC-02157 JLS (DFMx). This reference includes information regarding Össur's products that were on sale prior to the Nov. 15, 2019 priority date of the present application. Applicant requests that the Examiner consider the information describing details of Össur's products to have been described in a printed publication, or in public use, on sale, or otherwise available to the public, prior to the Nov. 15, 2019 priority date of the present application.

The Edinburgh Modular Arm System (EMAS), as described in the Edinburgh Modular Arm System (EMAS) Explanation of Relevance in 3 pages. Applicant requests that the Examiner consider this reference to have been described in a printed publication, or in public use, on sale, or otherwise available to the public, prior to the Nov. 15, 2019 priority date of the present application.

I-Limb and Pro-Digits products, on sale or in public use in the United States by May 31, 2007, including a photograph, engineering drawings and assembly instructions, as described in the i-Limb and Pro-Digits Explanation of Relevance in 19 pages.

I-Limb Shoulder, on sale in the United States at least as early as 2005, as described in the i-Limb Shoulder Explanation of Relevance in 2 pages.

Exhibit K1—Companies House as printed Jul. 27, 2016 in 1 page.
Exhibit K2—Department B Reproduction of the Current Contents of the Register Retrieval as dated Jul. 14, 2016 in 1 page.
Exhibit K3—Touch Bionics Limited, Directors' Report and Financial Statements, Dec. 31, 2015 in 64 pages.
Exhibit K4—EP 2 364 129 as published Jun. 19, 2013 in 12 pages.
Exhibit K5—Register Excerpt for file # 502009007405.0 as registered Dec. 9, 2016 in 4 pages.
Exhibit K6—Notice of Change of Name by Resolution as filed Jun. 12, 2014 in 4 pages.
Exhibit K7—Decision Rejecting the Opposition in European Application No. 09801137.2 as dated Mar. 23, 2016 in 8 pages.
Exhibit K8—WO 2007/063266 as published Jun. 7, 2007 in 30 pages.
Exhibit K9—Classification of Characteristics in 1 page.
Exhibit K10—Photographs 1-12 in 8 pages.
Exhibit K11—Drawings 1-3 in 2 pages.
Exhibit K12—i-digits™ quantum, Touch Bionics, Oct. 2015, 4 pages.
Exhibit K13—Touch Bionics, printed Nov. 20, 2016 in 4 pages.
Exhibit K14—Touch Bionics, printed Nov. 20, 2016 in 1 page.
Exhibit K15—Touch Bionics, Clinician Map, Germany, printed Aug. 11, 2016 in 1 page.
Exhibit K16—OTWORLD 2016 in 1 page.
Exhibit K17—OTWORLD—Overview, printed Nov. 2016 in 1 page.
Exhibit K18—Touch Bionics, Price List, Oct. 2015 in 18 pages.
Exhibit K19—Touch Bionics, i-digits quantum, dated Nov. 20, 2016 in 3 pages.
Exhibit K20—Touch Bionics, Document Library, dated Nov. 20, 2016 in 8 pages.
Exhibit K21—Touch Bionics, i-digits quantum, 2016 in 1 page.
Exhibit K22—Whols—Touch Bionics, printed Nov. 20, 2016 in 2 pages.
Exhibit K23—Denic, printed Nov. 20, 2016 in 3 pages.

* cited by examiner

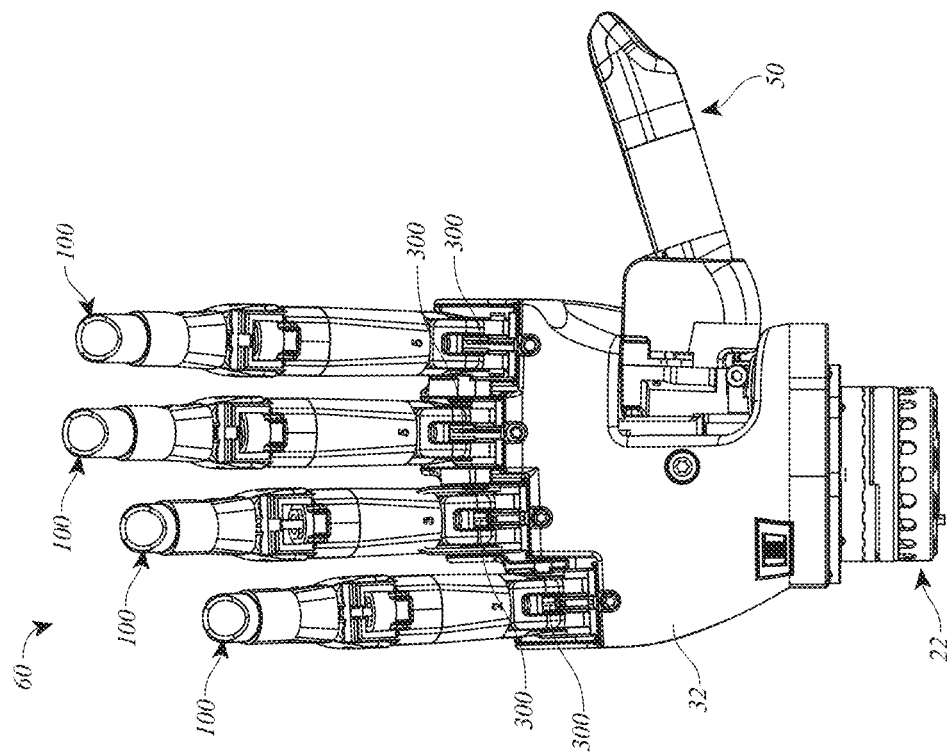
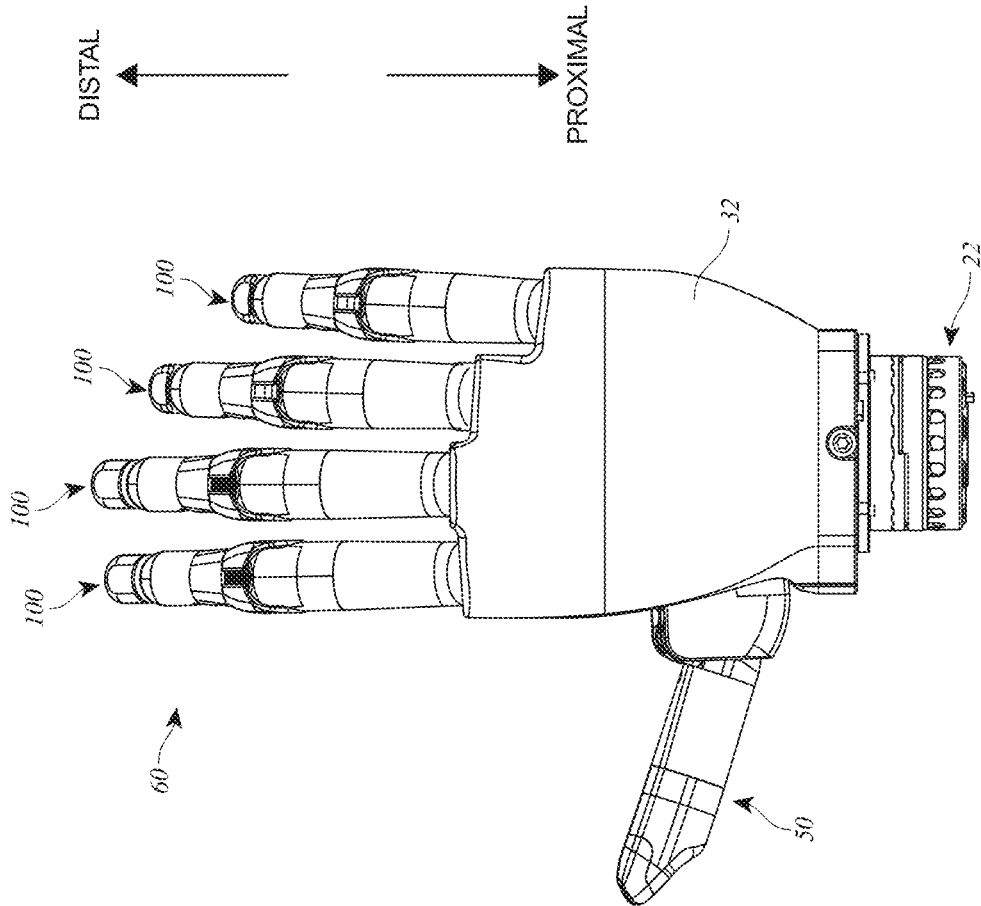

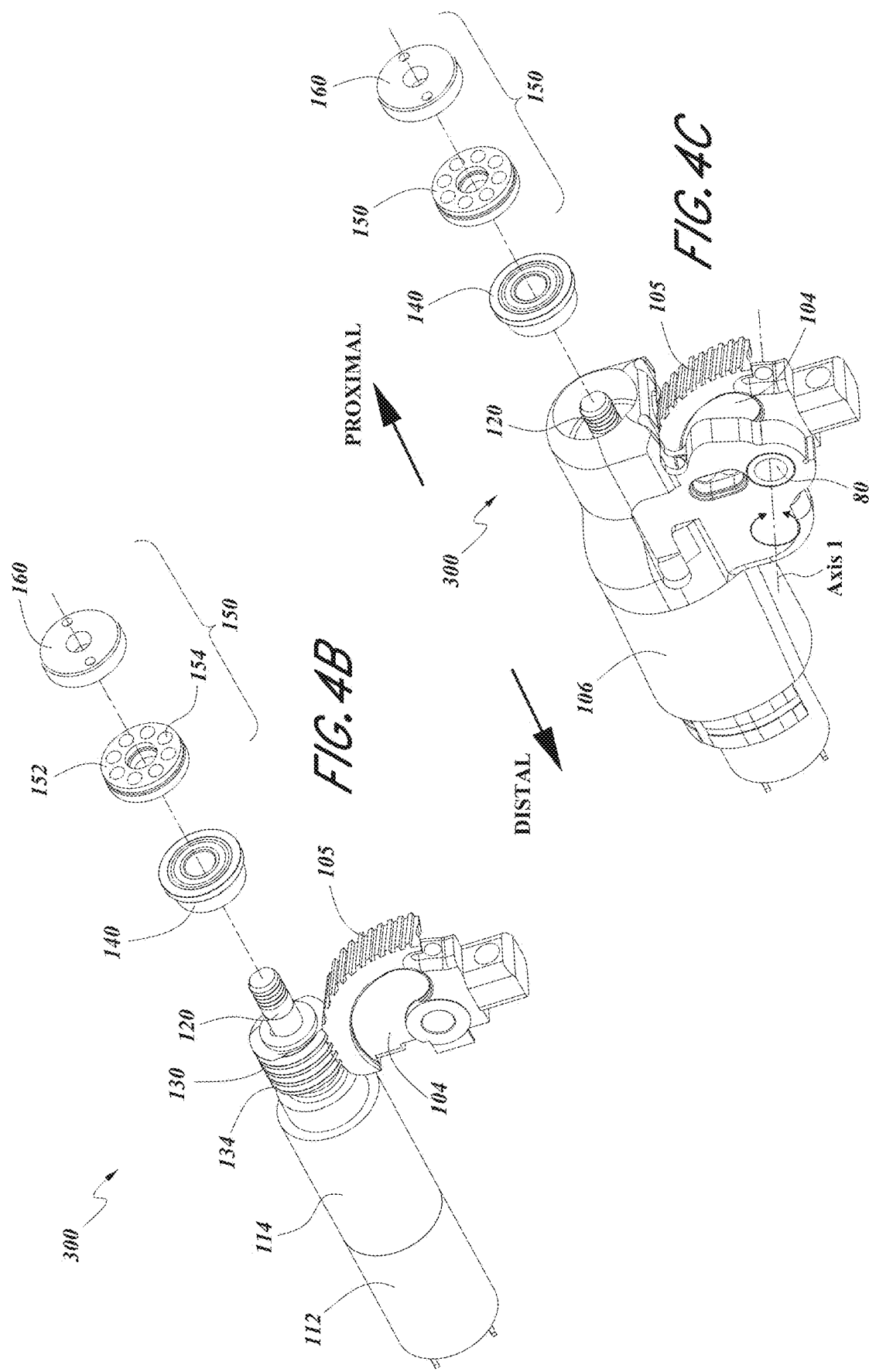

PROSTHETIC DIGIT ACTUATOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, the present application claims priority to U.S. Provisional Patent Application No. 62/935,852, titled "PROSTHETIC DIGIT ACTUATOR" and filed on Nov. 15, 2019, and U.S. Provisional Patent Application No. 63/064,614, titled "PROSTHETIC DIGIT ACTUATOR" and filed on Aug. 12, 2020, each of which is incorporated herein by reference in its entirety for all purposes and forms a part of this specification.

BACKGROUND

Field

The disclosure relates to prosthetic digits, in particular to actuators for prosthetic digits.

Description of the Related Art

Prosthetics are used to replace amputated natural body parts. Prosthetic digits may be used to replace amputated fingers and thumbs on a hand, or with prosthetic hands and/or arms. Existing solutions for prosthetic digits require large amounts of power and volume. Improvements to these and other drawbacks are desirable.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for prosthetic digit actuators.

The following disclosure describes non-limiting examples of some embodiments. Other embodiments of the disclosed systems and methods may or may not include the features described herein. Moreover, disclosed advantages and benefits can apply only to certain embodiments of the invention and should not be used to limit the disclosure.

Features for a prosthetic digit actuator are described. The various systems and methods allow for smaller volume actuators, which in turn allows for smaller digits and/or more space for other features of the digit. Such digits may be useful for smaller amputees having smaller hands, and for children with amputated digits and/or hands. The actuator includes a motor that causes rotation of a worm gear along a fixed worm wheel. A gearbox may be transmit the rotation. The worm gear is axially fixed along the output shaft. The worm gear climbs along the worm wheel to cause rotation of the digit and/or digit segment. A thrust bearing is located an on outer side of the worm gear relative to the motor along the shaft. A radial bearing is located between the worm gear and thrust bearing. The arrangement of the actuator parts allows for transmitting axial forces in first and second directions corresponding respectively to performing opening and closing rotations of the digits.

In one aspect, an actuator for a prosthetic digit is described. The actuator comprises a housing, a motor, an output shaft, a worm gear, a radial bearing, a thrust bearing, and a worm wheel. The motor is supported within the housing. The output shaft extends proximally along a rotation axis, where the motor is in mechanical communication with the output shaft and is configured to cause a rotation of the output shaft about the rotation axis. The worm gear is supported along the output shaft, and the worm gear is axially unsupported on a distal-facing side of a distal end of the worm gear, with the output shaft configured to cause rotation of the worm gear about the rotation axis, and the worm gear axially fixed on the output shaft. The radial bearing is supported along the output shaft proximally of the worm gear, with the radial bearing comprising an inner race in mechanical communication with an outer race, and the outer race in mechanical communication with the housing and rotationally fixed relative to the housing. The thrust bearing is supported along the output shaft proximally of the radial bearing, with the thrust bearing comprising a proximal race in mechanical communication with a distal race, the distal race in mechanical communication with and rotationally fixed relative to the outer race of the radial bearing, and the proximal race supported at a proximal end of the output shaft axially constraining the distal race and configured to rotate relative to the distal race, such that rotation of the output shaft rotates the distal race about the rotation axis. The worm wheel is configured to be attached with a prosthetic hand, where the worm wheel is in mechanical communication with the worm gear such that rotation of the worm gear about the rotation axis causes the worm gear to travel along an arcuate outer perimeter of the worm wheel.

Various embodiments of the various aspects are described. The actuator may further comprise a gearbox, where the motor is configured to rotate the output shaft via the gearbox. The inner race of the radial bearing may be in mechanical communication with the output shaft, and the output shaft may be configured to rotate the inner race relative to the outer race. The proximal end of the worm gear may be configured to transmit axial forces, due to actuation of the actuator, to a distal end of the inner race, which may transmit the axial forces via the outer race to the housing. The proximal race of the thrust bearing may be configured to transmit axial forces, due to actuation of the actuator, to the distal race of the thrust bearing, which may transmit the axial forces via the outer race of the radial bearing to the housing.

In another aspect, as actuator for a prosthetic digit is described. The actuator comprises a motor, an output shaft, a worm gear, a thrust bearing, and a worm wheel. The output shaft is located proximally of the motor, where the motor is configured to cause a rotation of the output shaft. The worm gear is supported along the output shaft, with the output shaft configured to cause rotation of the worm gear about the rotation axis. The thrust bearing is supported along the output shaft proximally of the worm gear. The worm wheel is in mechanical communication with the worm gear, where rotation of the worm gear about the rotation axis causes the worm gear to travel along an arcuate outer perimeter of the worm wheel.

Various embodiments of the various aspects are described. The worm gear may be axially unsupported on a distal-facing side of a distal end of the worm gear. The actuator may further comprise a gearbox in mechanical communication with the motor, where a space is located in between the gearbox and the distal end of the worm gear. The worm gear may be configured to remain axially fixed along the output shaft as the worm gear rotates. The worm gear may be bonded the output shaft. The actuator may further comprise a radial bearing supported along the output shaft in between the worm gear and the thrust bearing. A distal end of the radial bearing may contact a proximal end of the worm gear. The radial bearing may comprise an inner race and an outer race, with the inner race rotatable relative to the outer race, and where the inner race contacts the proximal end of the worm gear, and the outer race is rotationally stationary relative to the housing. The thrust bearing may comprise a distal race and a proximal race, with the distal race in mechanical communication with the radial bearing, and the proximal race configured to rotate relative to the distal race. The actuator may further comprise a cap supported along the output shaft proximally of the thrust bearing. The thrust bearing may comprise a distal race and a proximal race, and the cap may axially constrain the proximal race such that the cap and proximal race are configured to rotate together relative to the distal race. The actuator may further comprise a radial bearing supported along the output shaft in between the worm gear and the thrust bearing.

In another aspect, a prosthetic digit is described. The prosthetic digit comprises, a distal segment, a proximal segment. The proximal segment is rotatably attached to the distal segment and configured to rotatably attach to a prosthetic hand, with the proximal segment comprising a housing and an actuator. The actuator comprises a motor, a worm gear, a thrust bearing, and a worm wheel. The motor is configured to cause rotation of a proximally-extending output shaft. The worm gear is supported along the output shaft, with the output shaft configured to cause rotation of the worm gear about the rotation axis. The thrust bearing is supported along the output shaft proximally of the worm gear. Rotation of the worm gear causes the worm gear to travel along an arcuate outer perimeter of the worm wheel to rotate the proximal segment relative to the prosthetic hand.

Various embodiments of the various aspects, such as the prosthetic digit and other aspects, are described. The worm gear may be axially fixed relative to the output shaft. The worm gear may be bonded to the output shaft. The worm gear and the output shaft may be welded together. The worm gear and the output shaft may be unibody. The worm gear may be axially unsupported on a distally-facing side of a distal end of the worm gear. The prosthetic digit may further comprise a space located between the distally-facing side of the distal end of the worm gear and a proximal end of the motor. The prosthetic digit may further comprise a radial bearing located between the worm gear and the thrust bearing. The thrust bearing may comprise a distal race and a proximal race, with the proximal race configured to rotate with the output shaft relative to the distal race. The prosthetic digit may further comprise a gearbox, wherein the motor is configured to cause rotation of the output shaft via the gearbox. The worm gear may be axially unsupported on a distally-facing side of a distal end of the worm gear. The prosthetic digit further comprise a space located between the distally-facing side of the distal end of the worm gear and proximal end of the gearbox.

In another aspect, a prosthetic digit is described that comprises any of the actuators described herein.

In another aspect, a prosthetic hand is described that comprises any of the prosthetic digits described herein.

In another aspect, an actuator for a prosthetic digit is described. The actuator comprises a housing, a motor, an output shaft, a worm gear, a radial bearing, a thrust bearing, and a worm wheel. The housing is configured to be rotated relative to a prosthetic hand about a knuckle axis. The motor is supported within the housing. The output shaft is in mechanical communication with the motor, where the output shaft extends proximally along a rotation axis and has an outer thread located at a proximal end of the output shaft, where the motor is configured to cause a rotation of the output shaft about the rotation axis. The worm gear is axially fixedly supported along the output shaft and extending from a proximal end to a distal end with an outer threaded portion therebetween, with the distal end of the worm gear spaced axially from the proximal end of the motor to define a space adjacent to the distal end of the worm gear, with the output shaft configured to cause rotation of the worm gear about the rotation axis, and the worm gear configured to remain axially stationary along the output shaft as the worm gear rotates. The radial bearing is supported along the output shaft proximally of the worm gear, with the radial bearing comprising an inner race in mechanical communication with an outer race, the inner race in mechanical communication with the output shaft and configured to rotate relative to the outer race, and the outer race in mechanical communication with the housing and rotationally fixed relative to the housing. The output shaft is configured to rotate the inner race relative to the outer race, where the proximal end of the worm gear is configured to transmit axial forces due to actuation of the actuator to a distal end of the inner race which transmits the axial forces via the outer race to the housing. The thrust bearing is supported along the output shaft proximally of the radial bearing, with the thrust bearing comprising a proximal race in mechanical communication with a distal race. The distal race is in mechanical communication with and rotationally fixed relative to the outer race of the radial bearing, and the proximal race is configured to rotate relative to the distal race and is supported along the output shaft at the proximal end of the output shaft. The proximal race has an inner thread engaging the outer thread of the output shaft to axially constrain the distal race, such that rotation of the output shaft rotates the proximal race of the thrust bearing about the rotation axis. The worm wheel has outer teeth extending along an arcuate outer perimeter of the worm wheel and in mechanical communication with the outer threaded portion of the worm gear. The worm wheel is configured to be fixedly attached with a prosthetic hand, where rotation of the worm gear about the rotation axis causes the worm gear to travel along the arcuate outer perimeter of the worm wheel such that the housing, the motor, the output shaft and the worm gear rotate about the knuckle axis.

Various embodiments of the various aspects are described. The knuckle axis may be parallel to the rotation axis of the output shaft. The actuator may further comprise a gearbox, where the motor is configured to rotate the output shaft via the gearbox. The distal end of the worm gear may be spaced axially from a proximal end of the gearbox to define the space adjacent to the distal end of the worm gear.

In another aspect, an actuator for a prosthetic digit is described. The actuator comprises a housing, a motor, an output shaft, a radial bearing, a 4-point contact bearing, and a worm wheel. The motor is supported within the housing. The output shaft extends proximally along a rotation axis. The motor is in mechanical communication with the output shaft. The motor is configured to cause a rotation of the output shaft about the rotation axis. The output shaft includes a unibody worm gear axially fixed on the output shaft. The radial bearing is supported along the output shaft proximally of the worm gear. The radial bearing comprises an inner race in mechanical communication with an outer race. The outer race is in mechanical communication with the housing. The outer race is rotationally fixed relative to the housing. The 4-point contact bearing is located at a distal end of the output shaft distally of the worm gear. The 4-point contact bearing comprises at least one outer race and at least one inner race. The at least one outer race contacts a step on an inner sidewall of the housing that prevents distal translation of the 4-point contact bearing. The at least one inner race contacts the distal end of the output shaft. The at least one inner race is configured to rotate relative to the at least one outer race, such that rotation of the output shaft rotates the at least one inner race about the rotation axis. The worm wheel is configured to be attached with a prosthetic hand. The worm wheel is in mechanical communication with the worm gear such that rotation of the worm gear about the rotation axis causes the worm gear to travel along an arcuate outer perimeter of the worm wheel to thereby rotate the housing about the worm wheel.

Various embodiments of the various aspects are described. The actuator may further comprise a carrier shaft. The carrier shaft may extend proximally. The carrier shaft may be configured to engage the output shaft to mechanically transmit rotation from the motor to the output shaft. The output shaft may comprise an internal opening extending axially at least partially therethrough. The output shaft may be configured to at least partially receive the carrier shaft therein. The internal opening may comprise internal threads. The carrier shaft may comprise external threads configured to engage the internal threads. The actuator may further comprise a gearbox. The motor may be configured to rotate the output shaft via the gearbox. The at least one inner race may comprise two inner races. The at least one outer race may comprise two outer races. The two inner races may contact and rotate with the output shaft. The two outer races may be axially compressed by the housing and a preload ring.

In another aspect, an actuator for a prosthetic digit is described. The actuator comprises a housing, a motor, an output shaft, a first bearing, a second bearing, and a worm wheel. The motor is supported within the housing. The output shaft has a unibody worm gear. The output shaft extends proximally along a rotation axis. The motor is in mechanical communication with the output shaft. The motor is configured to cause a rotation of the output shaft about the rotation axis. The first bearing is located at a proximal end of the output shaft proximally of the worm gear. The second bearing is located at a distal end of the output shaft distally of the worm gear. The worm wheel is configured to be attached with a prosthetic hand. The worm wheel is in mechanical communication with the worm gear such that rotation of the worm gear about the rotation axis causes the worm gear to travel along the worm wheel to cause the housing and motor to rotate about the worm wheel.

Various embodiments of the various aspects are described. The actuator may further comprise a preload ring. The preload ring may be configured to axially constrain the second bearing. The housing may further comprise an inward step on a inner surface. The inward step may prevent axial movement of the second bearing in the distal direction. The first bearing may be a radial bearing. The first bearing may comprise an inner race in mechanical communication with an outer race. The outer race may be in mechanical communication with the housing. The outer race may be rotationally fixed relative to the housing. The second bearing may be a 4-point contact bearing. The second bearing may comprise at least one outer race and at least one inner race. The at least one outer race may contact a step on an inner sidewall of the housing that prevents distal translation of the 4-point contact bearing. The at least one inner race may contact the distal end of the output shaft. The at least one inner race may be configured to rotate relative to the at least one outer race, such that rotation of the output shaft rotates the at least one inner race about the rotation axis. Rotation of the worm gear about the rotation axis may cause the worm gear to travel along an arcuate outer perimeter of the worm wheel. The worm gear may be axially unsupported on a distal-facing side of a distal end of the worm gear. The worm gear may be axially unsupported on a proximal-facing side of a proximal end of the worm gear. The actuator may further comprise a gearbox in mechanical communication with the motor, where a space is located in between the gearbox and the distal end of the worm gear.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIGS. 2A-2B are back and front views, respectively, of a prosthetic hand incorporating embodiments of prosthetic digits, which prosthetic digits may be any of the prosthetic digits including any of the actuators described herein.

FIGS. 4A-4C are exploded views of the actuator of the prosthetic digit of FIGS. 1-3B.

DETAILED DESCRIPTION

Figure 1:
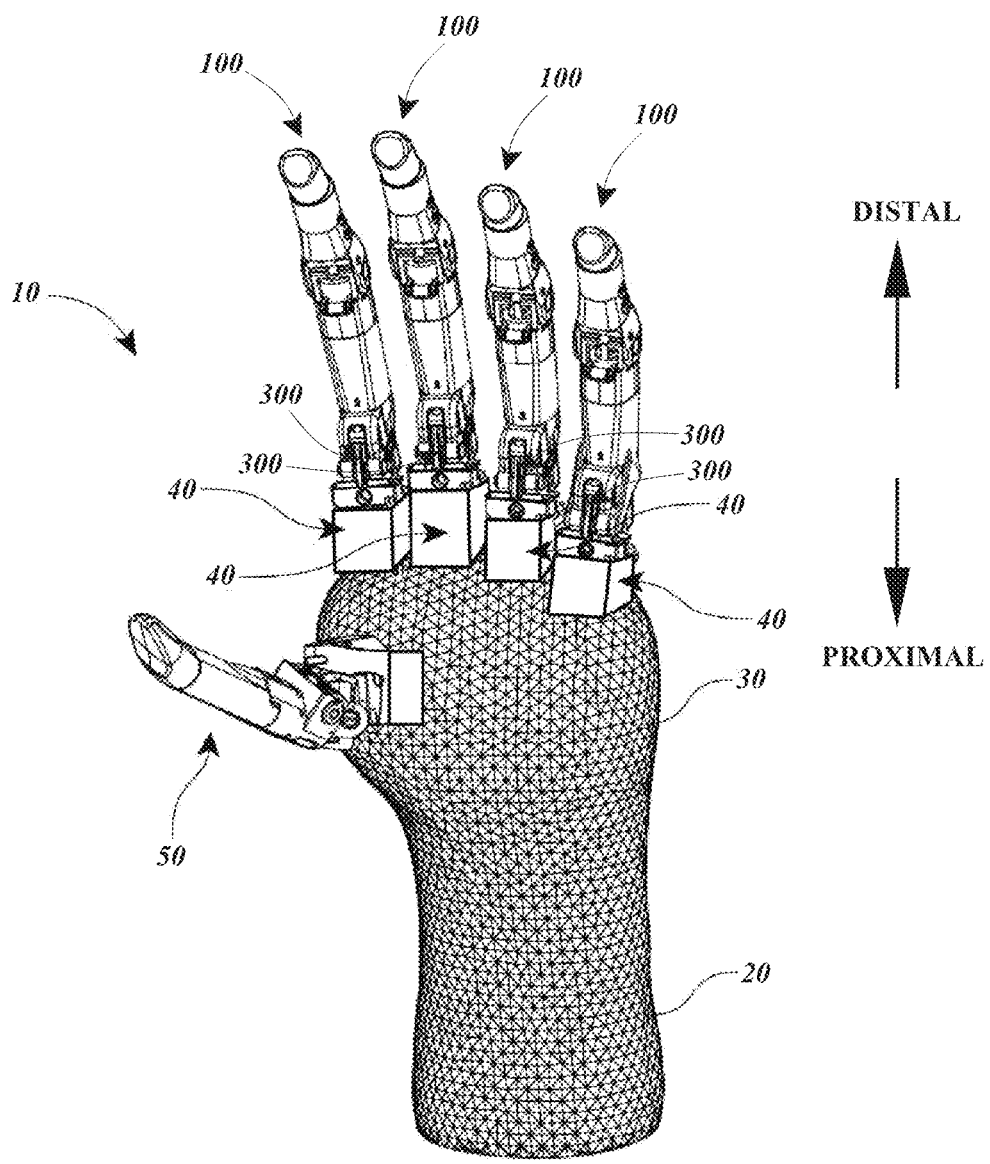
FIG. 1 is a front view of a lower arm stump having embodiments of prosthetic digits attached thereto, which prosthetic digits may be any of the prosthetic digits including any of the actuators described herein.

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

Features for prosthetic digit actuators are described. The actuator provides a drive mechanism where a worm wheel is fixed relative to a palm, and a housing via a rotated worm gear rotates around the worm wheel. A motor may rotate over the worm wheel via a gear box and shaft with the worm gear supported along the length of the shaft. The motor may be fixed with the housing, for example bonded or threaded and bonded with the housing. The worm gear is axially fixed, for example unibody, bonded or welded, to the shaft, for instance prior to gearbox assembly. "Unibody" as used herein refers to a monolithic piece, which for example could result from being machined from the same stock piece of raw material. Thus the shaft and worm gear may be a single piece component, for example machined from the same piece of metal.

In some embodiments, the worm gear is located in between the motor and a thrust bearing. The worm gear may be spaced from the motor or gearbox, for example spaced no less than 0.040 mm. The worm gear backs against a radial bearing, to allow for unloading first axial forces in a first direction away from the motor. These first axial forces may be due to rotation of the digit in a first direction, such as a closing rotation of the digit. The radial bearing transmits these first axial forces to the housing because an outer race of the radial bearing is fixed, e.g. bonded, to the housing. An end of the shaft is threaded and is thereby fixed to a proximal race of the thrust bearing, which may be a cap or nut. The proximal race unloads second axial forces in a second direction toward the motor which are opposite respectively to the first axial forces and direction. The second axial forces are unloaded to a distal race of the thrust bearing, which in turn unloads on the non-rotating element of the radial bearing, which unloads on the housing. The actuator may axially constrain the shaft so that no axial forces are transmitted to the motor/gearbox and no axial play is present. Axial play is eliminated by threading the proximal thrust bearing race to the shaft, for example during assembly.

The actuator has various uniquely desirable attributes. For example, the use of a thrust bearing reduces friction losses under axial load in the direction away from the motor, thus allowing faster digit closure compared to a plain bearing. As further example, the use of a thrust bearing located on the end of the shaft to deal with forces in the direction away from the motor is contrary to typical design practice. This is in contrast, for example, to a thrust bearing being located between the motor and the worm gear. The unique configuration described herein includes the worm gear being fixed to the shaft and the shaft being constrained axially. As further example, the configuration described herein minimizes the length of the digit. The configuration thus saves space and allows for a shorter and smaller digit, for example by not needing to accommodate the length of the thrust bearing in between the worm gear and the motor, and by having the shaft with the worm gear and bearings thereon extending toward the hand. These are just some example attributes, and others are described herein.

In some embodiments, as shown in FIGS. 10A-12, the actuator includes a distal bearing on a distal end of the output shaft and supporting the output shaft within the housing. The bearing may support the shaft radially, axially, or radially and axially. The bearing may be a 4-point contact bearing that provides both axial and radial support. A preload ring may secure the bearing within the housing. The worm gear may be unibody with the output shaft to form a "unibody shaft" and be located proximally of the distal bearing when the distal bearing is assembled onto the shaft. A proximal bearing may be located on a proximal end of the output shaft and support the output shaft. The proximal bearing may be a radial bearing. A proximal end of the output shaft may be internally threaded to mate with an external thread of a carrier shaft of the gear box. The embodiments of the prosthetic digit and actuator of FIGS. 10A-12 may include any of the features and/or functions as described with respect to the embodiments of the prosthetic digit and actuator of FIGS. 1-9B, and vice versa, except as otherwise stated explicitly or by context.

FIG. 1 is a front or palm-side view of a lower arm prosthetic system 10 including a lower arm stump 20, having four prosthetic digits 100 with an actuator 300 therein, and a prosthetic thumb 50, attached to the stump 20. The prosthetic digits 100 may be any of the prosthetic digits described herein and include any of the actuators described herein. In some embodiments, the thumb 50 may be any of the prosthetic digits described herein and include any of the actuators described herein. There may be one, two, three, four or more of the digits 100, with each digit 100 having any of the actuators described herein. The digits 100 may be connected to a residual natural palm 30, as shown in FIG. 1. In some embodiments, the digits 100 may be connected to the end of a lower arm stump 20, or to a prosthetic hand, or to a partial prosthetic hand. The digits 100 may include the actuator features described herein to provide small digits that take up smaller volumes compared to digits with other actuator features, among other advantages.

FIGS. 2A-2B are back and front views, respectively, of a prosthetic hand 60 incorporating the prosthetic digits 100 and the prosthetic thumb 50. The hand 60 has a palm portion 32 attached to proximal ends of the digits 100 and thumb 50. The hand 60 may have a wrist 22 that may rotate, which may allow for rotation of the palm portion 32, and the digits 100 and thumb 50 attached thereto, about a longitudinal axis defined by the wrist 22. The prosthetic digits 100 may be any of the prosthetic digits described herein and include any of the actuators described herein to cause rotation of the digits, such as opening and closing rotations of the digits or digit segments.

In some embodiments, the lower arm prosthetic system 10, the digits 100, the hand 60, the wrist 22, and the thumb 50 may include any of the features, respectively, for a lower arm prosthetic system, digits, hand, wrist, or thumb, described for example, in U.S. Provisional Patent Application No. 62/832,166, filed Apr. 10, 2019, and titled PROSTHETIC DIGIT WITH ARTICULATING LINKS, in U.S. Provisional Patent Application No. 62/850,675, filed May 21, 2019, and titled ACTUATION SYSTEMS FOR PROSTHETIC DIGITS, in U.S. Provisional Patent Application No. 62/902,227, filed Sep. 18, 2019, and titled PROSTHETIC DIGIT ACTUATORS WITH GEAR SHIFTING, in U.S. Provisional Patent Application No. 62/782,830, filed Dec. 20, 2018, and titled ENERGY CONSERVATION OF A MOTOR-DRIVEN DIGIT, in U.S. patent application Ser. No. 16/011,108, filed Jun. 18, 2018, and titled PROSTHETIC DIGIT FOR USE WITH TOUCHSCREEN DEVICES, in U.S. patent application Ser. No. 14/765,638, filed Aug. 4, 2015, and titled MULTI-MODAL UPPER LIMB PROSTHETIC DEVICE CONTROL USING MYOELECTRIC SIGNALS, in U.S. patent application Ser. No. 16/423,802, filed May 28, 2019, and titled WRIST DEVICE FOR A PROSTHETIC LIMB, in U.S. patent application Ser. No. 16/204,059, filed Nov. 29, 2018, and titled SYSTEMS AND METHODS FOR PROSTHETIC WRIST ROTATION, in U.S. Provisional Patent Application No. 62/599,559, filed Dec. 15, 2017, and titled POWERED PROSTHETIC THUMB, in U.S. patent application Ser. No. 16/249,696, filed Jan. 16, 2019, and titled SYSTEMS AND METHODS FOR CONTROLLING A PROSTHETIC HAND, the entirety of each of which is incorporated by reference herein for all purposes and forms part of this specification.

Figure 3A:
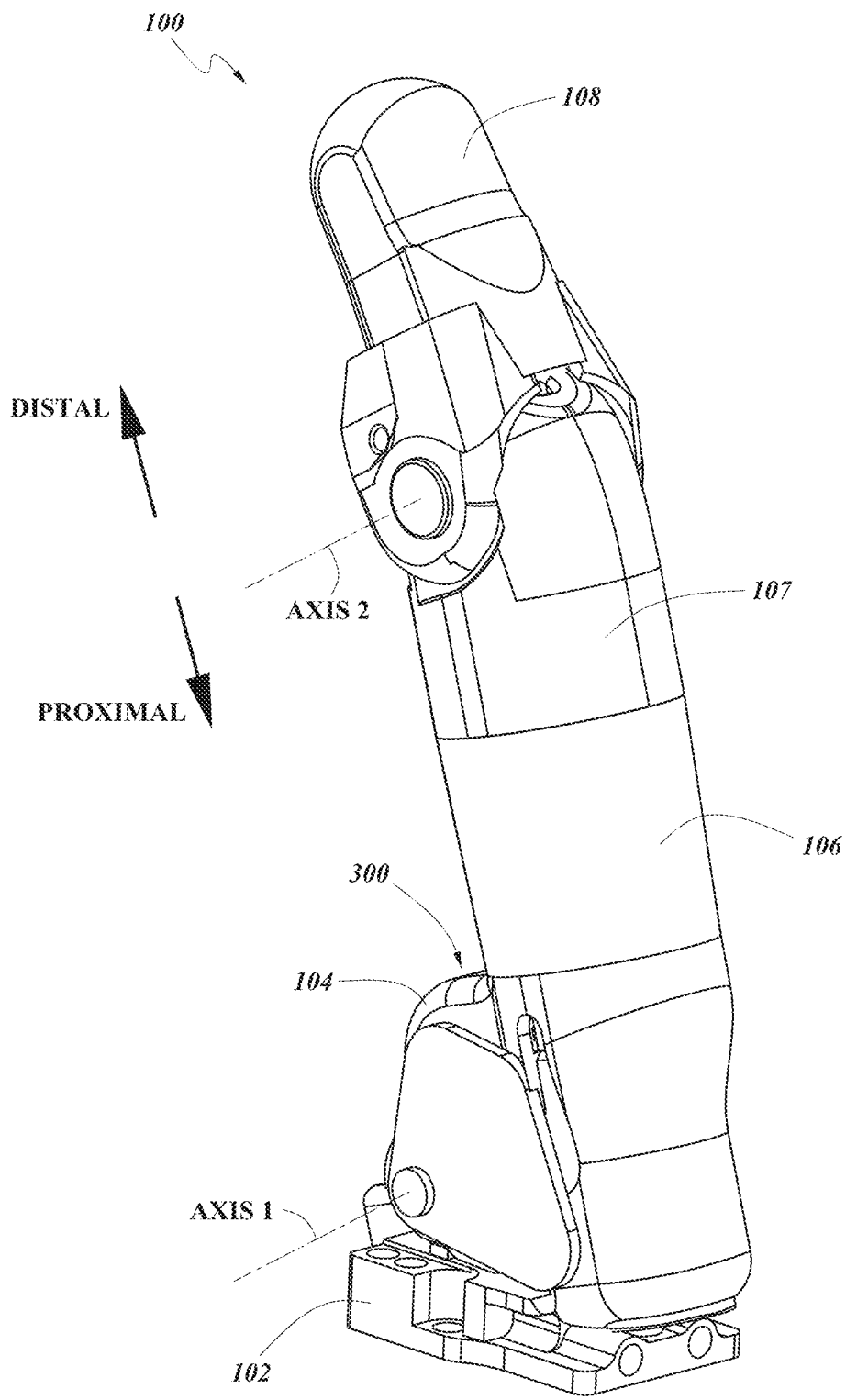
FIGS. 3A-3B are rear and front perspective views respectively of the prosthetic digit of FIGS. 1-2B having an actuator therein.
Figure 3B:
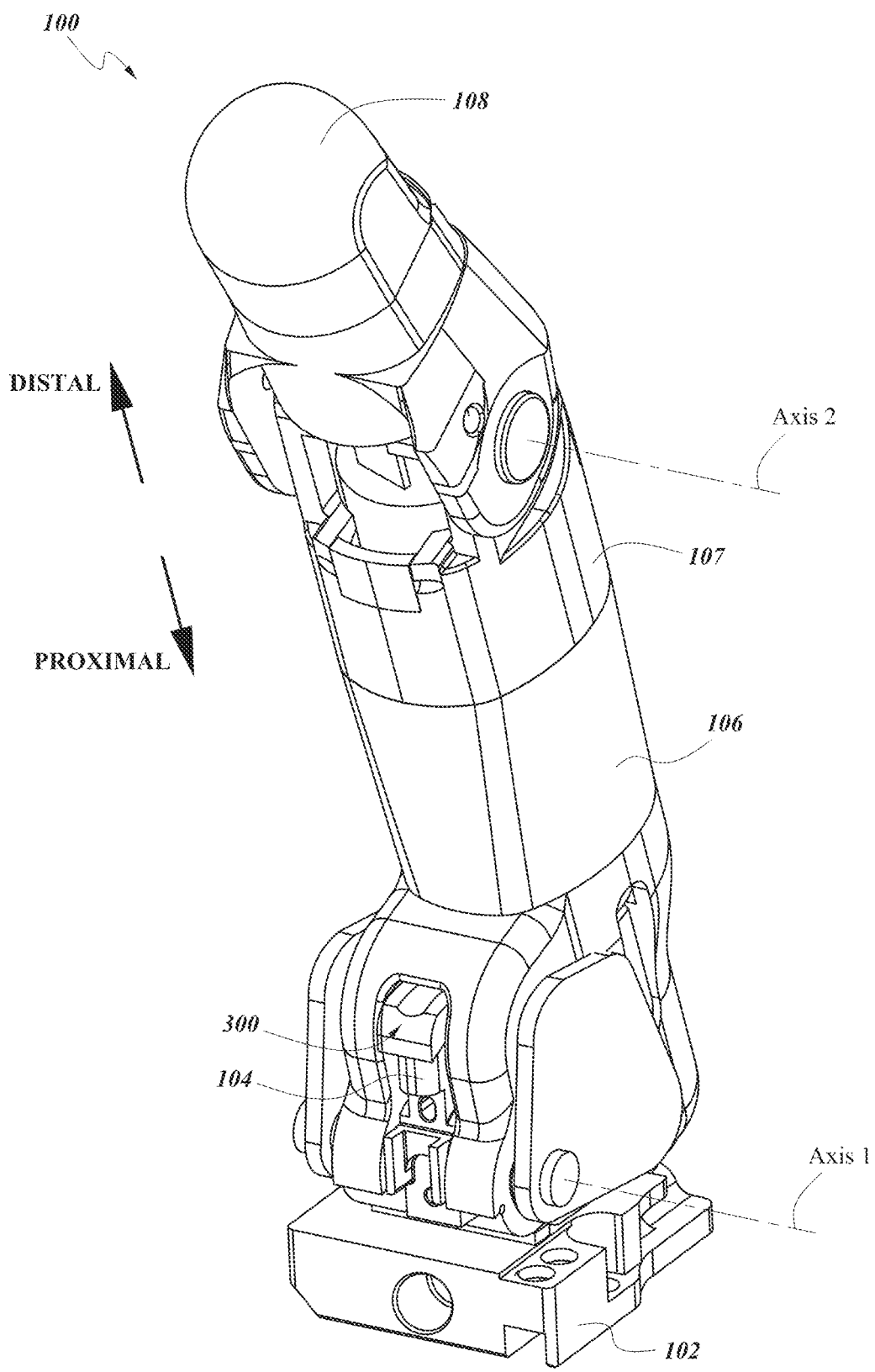

FIGS. 3A-3B are rear and front perspective views, respectively, of the prosthetic digit 100 having the actuator 300. The actuator 300 includes a worm wheel 104, which is partially visible, and is further described herein, for example with respect to FIGS. 4A-7D. As shown in FIGS. 3A-3B, the digit 100 may be described using "proximal" and "distal" directions. Proximal refers to a direction generally toward the hand and away from the tip of the digit 100. Distal refers to a direction generally toward the tip of the digit 100 and away from the hand. For reference, a hand may attach at a base 102 of the digit 100, and at the tip of the digit 100 there may be a distal segment 108. The digit 100 may be used as a small digit compared to typical sized prosthetic digits. The digit 100 may have an overall length as measured in a straight line from a proximal end of the base 102 or from the Axis 1, to a distal tip of the distal end of the digit 100, such as at the distal end of the distal segment 108, with the digit segments fully straightened. This length may be from about 30-90 mm long, from about 40-80 mm long, from about 50-70 mm long, or from about 55-65 mm long.

The digit 100 includes the base 102 at a proximal end thereof. The base 102 is configured to attach to a hand, such as a prosthetic, partial-prosthetic, or natural hand. The digit 100 includes a housing 106, which may be a proximal segment of the digit 100, rotatably attached to the base 102 about a first axis 1. Actuation of the actuator 300 causes the housing 106 to rotate about the first axis 1. The worm wheel 104 remains stationary as the housing 106 rotates about the worm wheel 104. The digit 100, for example the housing 106, may include a distal portion 107 at a distal end of the housing 106. The digit 100 includes a distal segment 108 rotatably attached to the distal portion 107 about a second axis 2. A distal end of the distal portion 107 is attached to a proximal end of the distal segment 108. The segments 106, 108 may rotate relative to each other about the second axis 2. In some embodiments, there may be one, three or more rotatable segments of the digit 100, with one, three or more rotation axes per digit 100. The distal portion 107 may be a separate component of the housing 106 that is attached together or these may be a single structure. The housing 106 may be relatively small compared to typical digits, for example for use with a small or a extra small digit 100. The housing 106 may be from about 10-20 mm in width, from about 12-18 mm in width, or from about 14-16 mm in width. The width may be measured perpendicular to a longitudinal axis of the housing 106, said axis shown for example in FIGS. 4B and 4C. The housing 106 may be from about 30-60 mm long, from about 35-55 mm long, or from about 40-50 mm long. The length may be measured along the longitudinal axis from a proximal end to a distal end of the housing 106.

Figure 4A:
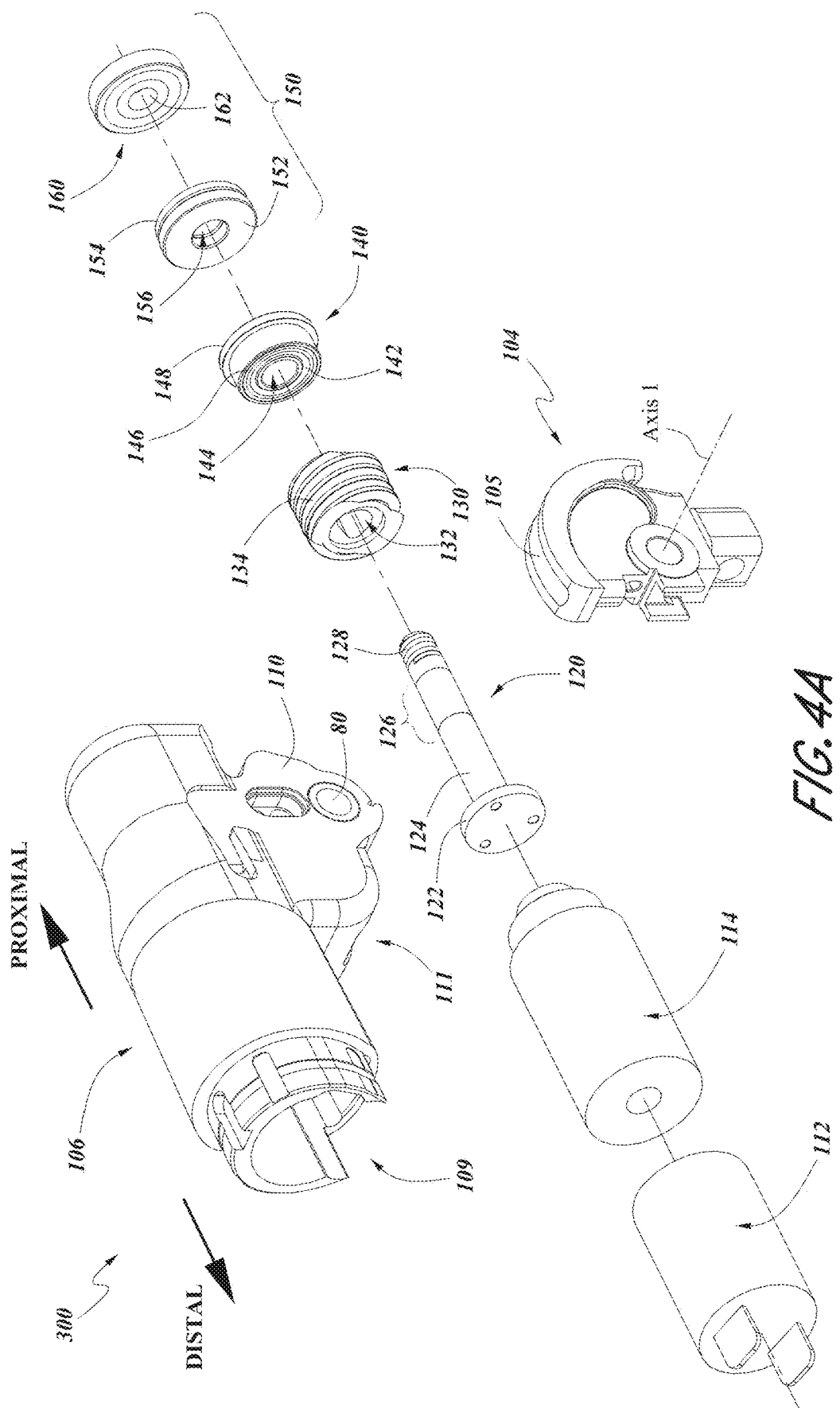

FIGS. 4A-4C are exploded views of an embodiment of the actuator 300. FIG. 4A shows a fully exploded view of the actuator 300, and FIGS. 4B and 4C show partial exploded views of the actuator 300. The actuator 300 includes the housing 106 defining an opening 109 therein. The opening 109 may receive the various components of the actuator 300 therein, and provide structural cover. The housing 106 includes a clevis 110 with two projections extending outward therefrom, for example perpendicular to a longitudinal axis defined by the opening 109, and defining a space 111 between the two projections. The two projections of the clevis 110 each include an opening 80 extending therethrough, which can receive a bushing or axle to provide rotation about the first axis 1. The opening 109 may have various inner widths to accommodate the various parts therein. The opening 109 may have a maximum inner width, e.g. a maximum inner diameter, from about 6-14 mm, from about 8-12 mm, or from about 9-11 mm.

The actuator 100 includes the worm wheel 104, which may be partially shaped as a lug or other projection. The worm wheel 104 attaches at a proximal end to the base 102. The worm wheel 104 has an upper portion as oriented in the figure that extends arcuately with a series of teeth 105 thereon. The teeth 105 provide a structure over which a worm gear 130 can engage and travel or climb to effectuate rotation about the first axis 1. The worm wheel 104 may be received into the space 111 defined by the clevis 110 when assembled. The teeth 105 may extend along a circular or other rounded path. The teeth 105 may extend for about ninety degrees about the first axis 1, or other angular amounts. The first axis 1 may be in other locations. The first axis 1 may be fixed, for example where the teeth 105 extend along a circular path. In some embodiments, the first axis 1 may move, for example where the teeth 105 extend along a non-circular, such as an oval or elliptical, path.

The actuator 300 includes a motor 112 and a gearbox 114. The motor 112 may be an electric motor electrically connected to a power source, such as batteries. The motor 112 may be a brushed, brushless, and/or a direct current motor, such as those manufactured by Maxon Motor AG (Switzerland). The gearbox 114 may be a variety of different suitable gearboxes. The motor 112 attaches to the gearbox 114 to provide rotation of a shaft 120, such as an output shaft. The shaft 120 is an elongated structure extending proximally from the motor. The shaft 120 may be rotated at constant or varying torque and/or speed. In some embodiments, there may just be the motor 112 without the gearbox 114. The gearbox 114 may transmit rotation from the motor 112 to the shaft 120, for example to provide a desired torque and/or speed of rotation of the shaft 120. A distal end of the shaft 120 attaches to a proximal end of the gearbox 114. The shaft 120 includes a head 122 at a distal end thereof that forms a disc-like flange. A smaller-diameter shaft portion 124 extends proximally from the head 122 and toward the palm when assembled with a hand. The shaft portion 124 is an elongated structure extending proximally from a proximal end of the motor. The shaft portion 124 may extend from about 16-18 mm, or about 17.6 mm, from a proximal end of the motor 112 to a proximal end tip of the shaft portion 124. The shaft portion 124 may extend 10 mm or less, 15 mm or less, 17 mm or less, 19 mm or less, 21 mm or less, or 25 mm or less, from a proximal end of the motor 112 to a proximal end tip of the shaft portion 124. The shaft portion 124 may be about 3 mm in width, e.g. diameter. The shaft portion may be from about 1.5 to about 4.5 mm, from about 2 mm to about 4 mm, or from about 2.5 mm to about 3.5 mm in width. These widths may refer to a diameter of a portion of the shaft portion 124 having a circular cross-section, and/or to a width of a portion thereof having a non-circular cross-section.

The elongated shaft portion 124 includes a first attachment area 126, along which the worm gear 130 may be supported. The worm gear 130 may be fixedly attached to the shaft portion 124 at the first attachment area 126, as further described herein. The first attachment area 126 may be a location along the shaft portion 124 at which the worm gear 130 and/or other components are positioned. The first attachment area 126 may be located closer to the proximal end of the shaft portion 124 than to the head 122, in the middle of the length of the shaft portion 124, or closer to the head 122 than to the proximal end. The first attachment area 126 may have similar or different surface features as the shaft portion 124 adjacent the head 122. The first attachment area 126 may include threads, projections, modified surface roughness, other suitable features, or combinations thereof. The shaft portion 124 adjacent the head 122 may have a circular or other rounded cross-sectional shape. The first attachment area 126 may have a non-circular cross-sectional shape. For example, as further described herein for instance with respect to FIG. 6, the first attachment area 126 may have a "D" cross-sectional shape, with a flat edge and a rounded edge. In some embodiments, the first attachment area 126 may have a circular or other rounded cross-sectional shape.

The shaft portion 124 includes a second attachment area 128 at a proximal end of the shaft 120. The second attachment area 128 may include threads, as shown, and/or other attachment features. The second attachment area 128 may have any of the cross-sectional shapes as described herein with respect to the first attachment area 126. The second attachment area 128 may have the same or similar cross-sectional shape as the first attachment area 126, such as the "D" cross-section. In some embodiments, the second attachment area 128 may have a different cross-sectional shape from the first attachment area 126. A proximal race 160 of a thrust bearing 150 may be attached at the second attachment area 128, as further described herein.

The actuator 300 includes the worm gear 130. The worm gear 130 has a rounded outer cross-sectional shape and extends from a proximal end to a distal end with an outer thread 134 extending around the body. The thread 134 may extend completely or partially between the distal and proximal ends. The thread 134 is configured to mechanically communicate with, for example directly engage, the teeth 105 of the worm wheel 104.

The worm gear 130 defines an axial opening 132 extending therethrough. The opening 132 receives the shaft 120 therein. The opening 132 may have any of the cross-sectional shapes as described herein with respect to the first attachment area 126. The opening 132 may have inner surfaces with an inner cross-sectional shape that corresponds to an outer cross-sectional shape of outer surfaces of the first attachment area 126. The opening 132 may thus have a "D" shaped cross-section to match with a "D" shaped cross-section of the firsts attachment area 126. The cross-sections, such as the "D" cross-section, may correspond in order to transfer rotation of the shaft 120 to the worm gear 130. The "D" cross-section is merely one example and other shapes may be used to transfer such rotation. Further details of the worm gear 130 are described herein, for example with respect to FIGS. 7A-7D.

The worm gear 130 is supported by the shaft portion 124, which may be at the first attachment area 126. The worm gear 130 may be bonded to the shaft 120. The worm gear 130 may have an interference fit with the shaft 120. The worm gear 130 may be bonded to the shaft 120, welded with the shaft 120, laser-welded with the shaft 120, interference fitted with the shaft 120, have other suitable mechanical attachment methods with the shaft 120, or combinations thereof, to remain axially fixed on the shaft portion 124. The various mechanical attachment methods may be incorporated at the first attachment area 126. The worm gear 130 may be unibody with the shaft 120, such that the worm gear 130 and the shaft 120 form a single, monolithic part. The worm gear 130 may be fixed at a location along the shaft portion 124 such that a gap is defined between a distal-facing side of the worm gear 130 and an adjacent structure such as the gearbox 114 or the motor 112, as further described herein, for example with respect to FIG. 5.

The actuator 300 includes a radial bearing 140. The radial bearing 140 is located proximally of the worm gear 130. The radial bearing 140 may be a variety of suitable radial bearings configured to transmit radial and/or axial forces from the shaft 120 and/or worm gear 130 to the housing 106. The radial bearing 140 includes an inner race 142 surrounded radially by an outer race 146. The inner and outer races 142, 146 may rotate relative to each other about a longitudinal axis defined by the bearing 140. A series of balls may be located arcuately between the races 142, 146, for example in a radial ball bearing. The inner and outer races 142, 146 may have circular or other rounded inner and outer cross-sectional shapes. The inner race 142 surrounds outer surfaces of the shaft 120 and the outer race 146 is surrounded by inner surfaces of the housing 106. The bearing 140 thus stabilizes the shaft 120 along the length of the shaft 120 and provides for stable rotation of the shaft 120, among other functions. The radial bearing 140 may have an outer diameter, e.g. of the outer race 146, of about 7 mm. This outer diameter may be from about 5 mm to about 9 mm, from about 6 mm to about 8 mm, or from about 6.5 mm to about 7.5 mm.

The inner race 142 defines an opening 144 therethrough. The opening 144 may define the longitudinal axis about which the races 142, 146 rotate relative to each other. The opening 144 is configured to receive a portion of the shaft 120 therein such that the shaft 120 supports the bearing 140 along the length of the shaft portion 124. The opening 144 may thus receive the shaft portion 124 therein. The opening 144 may have a circular cross-sectional shape. The opening 144 may have any of the cross-sectional shapes as described herein with respect to the first attachment area 126, such as "D" shape, etc. The opening 144 may be located at a distal portion of the shaft portion 124. The inner race 142 may be located at or near the first attachment area 126. The inner race 142 may be located proximally of the first attachment area 126. The inner race 142 may be in other locations along the length of the shaft 120.

The inner race 142 may have a transitional fit with the shaft portion 124. For example, the inner race 142 may be fitted with the shaft portion 124 by hand. The fit between the inner race 142 and the shaft 124 may not allow for any free relative movement, such as axial, rotational, and/or radial movement, between the inner race 142 and the shaft 124. The inner race 142 may have a transitional fit with the shaft 120, be bonded to the shaft 120, be attached in other suitable mechanical ways to the shaft 120, or combinations thereof. As further described herein, for example with respect to FIG. 5, a distal end of the inner race 142 contacts a proximal end of the worm gear 130 to transmit axial forces in the proximal direction to the housing 106 via the outer race 146. As further described herein, for example with respect to FIG. 5, as the shaft 120 rotates, the inner race 142 may rotate with the shaft 120 and relative to the outer race 146.

The outer race 146 may include a flange 148 at a proximal end thereof. The flange 148 may protrude radially outwardly from the outer race 146. The flange 148 may have a circular or other rounded cross-sectional shape, or other shapes. The outer race 146 may be partially received into a portion of the housing such that a distal side surface of the flange 148 contacts a proximal-facing surface of the housing 106, as further described herein, for example with respect to FIG. 5. The flange 148 may transmit axial forces in the distal direction to the housing 106. A distal end of the outer race 146 may not contact the worm gear 130. As further described, the outer race 146 may be rotationally stationary with respect to the housing 106.

The actuator 300 includes the thrust bearing 150. The thrust bearing 150 is positioned or located proximally of the worm gear 130 and radial bearing 140. The worm gear 130 is thus located in between the gearbox 114 and the thrust bearing 150. The worm gear 130 may be located in between the motor 112 and the thrust bearing 150. By locating the thrust bearing proximally of the worm gear 130, less volume is needed compared to a digit that locates a thrust bearing between the worm gear 130 and the gearbox 114. The digit 100 may thus have a smaller overall length. The fixed worm wheel 104 in conjunction with the proximal location of the thrust bearing 150, and other features of the actuator 300 described herein, contributes to the smaller volume and the other advantages as further described.

The thrust bearing 150 includes a distal race 152 and a proximal race 160. The distal race 152 is separate from and rotates relative to the proximal race 160 via a set of caged balls 154 (see FIG. 5) spaced arcuately therebetween. The caged balls 154 may attach to the proximal race 160. The thrust bearing 150 may be a variety of suitable thrust bearings configured to primarily absorb axial loads, or loads generally along the proximal/distal directions. The thrust bearing 150 transmits such axial loads during rotation of the digit 100, as further described herein, for example with respect to FIG. 5.

The distal race 152 defines an opening 156 therethrough. The proximal race 160 defines an opening 162 therethrough. The openings 156, 162 are configured to align with each other and to receive a proximal end of the shaft 120 therein. The opening 156 may be smooth and be located proximally and adjacent to the first attachment area 126 of the shaft 120. The opening 162 may be internally threaded and be located at the second attachment area 128 of the shaft 120 to engage corresponding outer threads of the second attachment area 128. When assembled, the distal race 152 contacts the outer race 146 of the radial bearing 140, and the proximal race 160 rotates with the shaft 120 relative to the distal race 152 via the caged balls 154, as further described herein, for example with respect to FIG. 5. The opening 162 of the proximal race 160 may threadingly engage the second attachment area 128, be bonded to the second attachment area 128, be mechanically attached in other suitable ways with the second attachment area 128, or combinations thereof.

In some embodiments, the proximal race 160 may be a cap or nut having an internal thread and that is configured to rotate relative to the distal race 152 via the caged balls located therebetween. For example, an internally threaded nut, a circular disc with an internal thread, or other suitable component may be used as the proximal race 160.

FIG. 4B is a partially exploded view of the actuator 300. The motor 112, gearbox 114, shaft 120, worm gear 120, and worm wheel 104 are assembled together. The radial bearing 140 and thrust bearing races 152, 160 are shown in exploded view and may be positioned onto the shaft 120 as described herein. FIG. 4C depicts the actuator 300 of FIG. 4B with the housing 106. The housing 106 covers the gearbox 114, worm gear 130, and shaft 120. The bearings 140, 150 attach to the shaft 120 and are also located inside the housing 106 when assembled, as more clearly shown in FIG. 5. As the digit 100 rotates, the housing 106, motor 112, gearbox 114, shaft 120, worm gear 120, and bearings 140, 140 rotate together about the first axis 1 as the worm gear 120 travels along the teeth 105 of the worm wheel 104.

Figure 5:
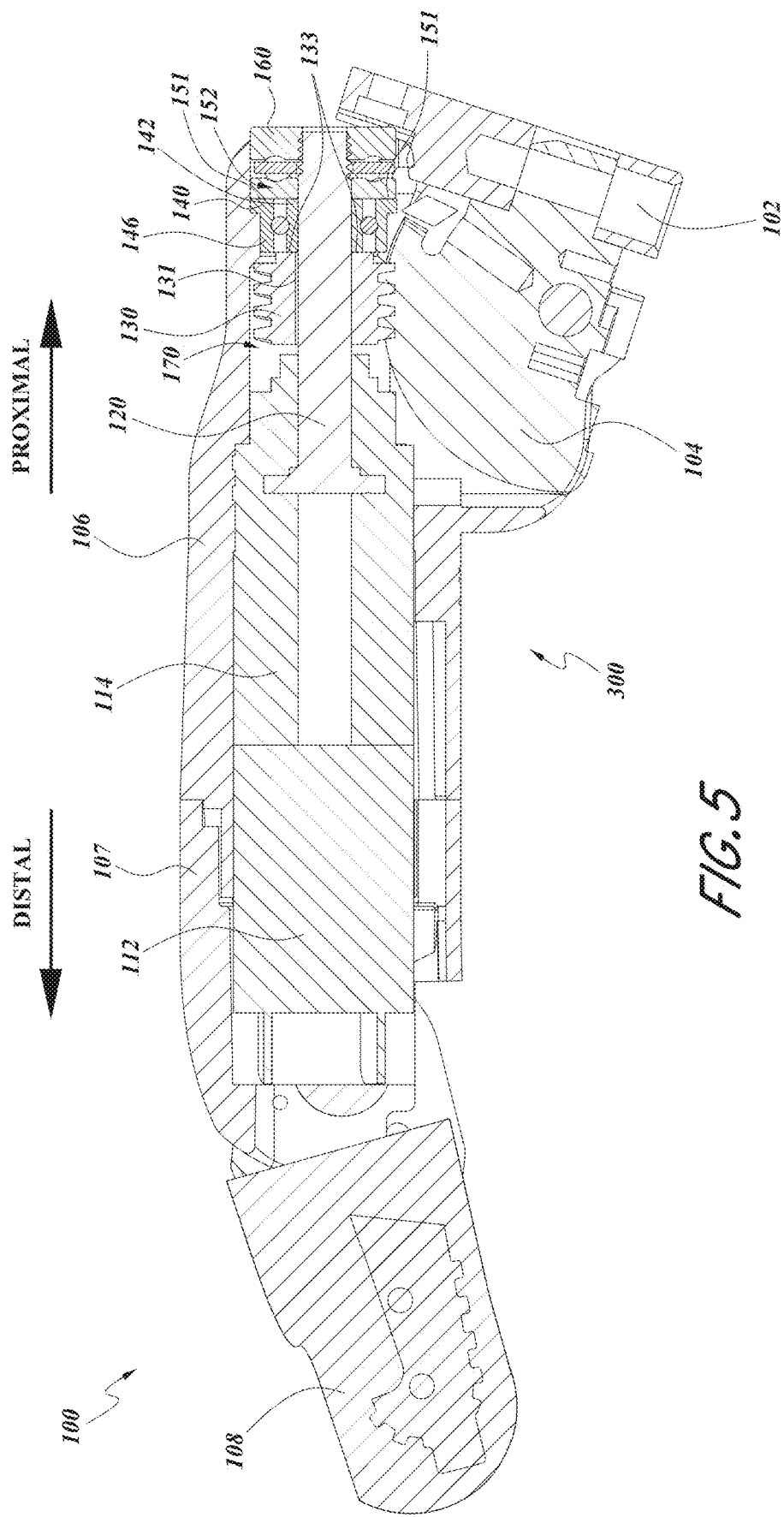
FIG. 5 is a side cross-section view of the prosthetic digit of FIGS. 1-3B.

FIG. 5 is a side cross-section view of the prosthetic digit 100 including the actuator 300 assembled together. The motor 112 may be located within the distal portion 107 that is attached to the housing 106. The housing 106 and/or distal portion 107 may form a proximal segment of the digit 100. The distal portion 107 may rotate with the housing 106. The distal portion 107 may be removably attached to the housing 106 for ease of assembly and maintenance. The distal segment 108 may be rotatably attached to the distal portion 107 of the proximal segment 106. The distal portion 107 may have an opening therethrough, which may correspond to and continue the opening 109 of the housing 106.

As shown, a distal end of the inner race 142 of the radial bearing 140 contacts a proximal end of the worm gear 130 at a contact area 133. The contact area 133 may be a rounded, for example circular, surface area and extend about the longitudinal axis of the bearing 140. The worm gear 130 may transmit axial forces in the proximal direction to the housing 106 via the contact area 133. For example, as the digit 100 performs a closing rotation, such that the worm gear 130 travels counterclockwise relative to the worm wheel 104 as oriented in FIG. 5, the worm wheel 104 exerts axial forces on the worm gear 130 in the proximal direction. These proximal axial forces are then transmitted from the worm gear 130 to the inner race 142 via the contact area 133. The inner race 142 then transmits the forces via the balls of the bearing 140 to the outer race 146, which is in contact with the inner surface of the housing 106 and so transmits the forces to the housing 106. In this manner, axial forces in the proximal direction are transmitted to the housing 106. Further, these proximal axial forces are transmitted as the shaft 120 rotates because the inner race 142 may rotate with the shaft 120 and relative to the outer race 146. The outer race 146 may be rotationally stationary relative to the housing 106. The distal end of the outer race 146 may not contact the worm gear 130.

As further shown in FIG. 5, a distal-facing surface of the distal race 152 of the thrust bearing 150 contacts a proximal-facing surface of the proximal end of the outer race 146 of the radial bearing 140 at a contact area 151. The contact area 151 may be rounded, for example circular, and extend about the longitudinal axis of the bearing 150. The thrust bearing 150 may transmit axial forces in the distal direction to the housing 106 via the contact area 151. As the digit 100 performs an opening rotation, such that the worm gear 130 travels clockwise relative to the worm wheel 104 as oriented in FIG. 5, the worm wheel 104 exerts axial forces on the worm gear 130 in the distal direction. These distal axial forces are then transmitted from the worm gear 130 to the proximal race 160 of the thrust bearing 150 via the shaft 120. The proximal race 160 then transmits the forces via the balls of the bearing 150 to the distal race 152, which is in contact with the outer race 146 of the radial bearing 140 at the contact area 151, and so transmits the forces to the housing 106 via the flange 148 of the radial bearing 140.

In this manner, axial forces in the distal direction are transmitted to the housing 106. Further, these distal axial forces are transmitted as the shaft 120 rotates because the proximal race 160 rotates with the shaft 120 and relative to the distal race 152. The distal race 152 may be rotationally stationary relative to the outer race 146. The distal-facing surface or surfaces of the distal race 152 may be compressed against the proximal-facing surface or surfaces of the outer race 146. The elimination of axial play in the assembled components may cause such contact and compression. In some embodiments, the distal race 152 is bonded to the outer race 146 and/or housing 106, is mechanically attached in other suitable ways to the outer race 146 and/or housing 106, or combinations thereof. The distal race 152 may not contact the inner race 142 of the radial bearing 140. There may be a groove or recess in the distal-facing surface of the distal race 152, and/or the inner race 142 may extend proximally but stop short of contacting the distal-facing surface of the distal race 152.

The actuator 300 may include a space 170. The space 170 may be a gap, opening, empty volume, or the like. The space 170 may be located on a distal side of the distal-facing surfaces of the distal end of the worm gear 130. The space 170 may be between the worm gear 130 and the gearbox 114. The worm gear 130 may thus be unsupported on a distal-facing end of the worm gear 130. The worm gear 130 may be axially fixed such that the space 170 remains while the shaft 120 is rotating and while stationary. The space 170 as measured axially, or as measured parallel to distal and proximal directions, between the proximal-most end of the gearbox 114 and the distal-most end of the worm gear 130 may be greater than or equal to 0.040 millimeter (mm). In some embodiments, the space 170 measured as described may be greater than or equal to 0.010 mm, greater than or equal to 0.020 mm, greater than or equal to 0.030 mm, greater than or equal to 0.035 mm, greater than or equal to 0.045 mm, greater than or equal to 0.050 mm, greater than or equal to 0.060 mm, greater than or equal to 0.080 mm, greater than or equal to 0.10 mm, or greater than or equal to 0.20 mm. In some embodiments, the space 170 may have other configurations, as described in further detail herein, for example with respect to FIGS. 8A-9B.

Figure 6:
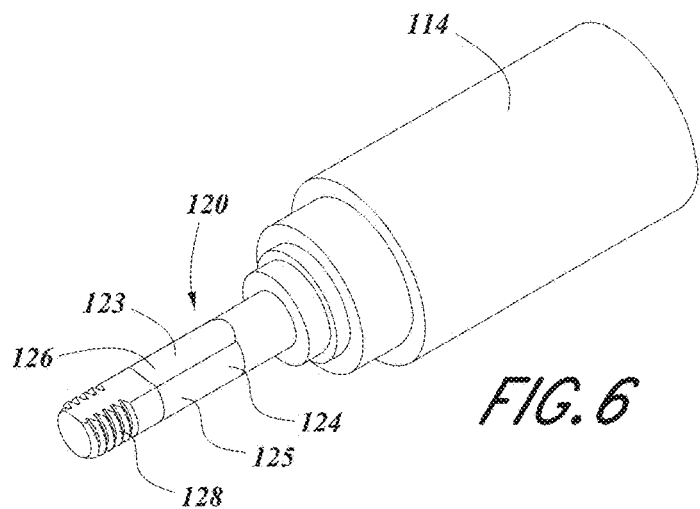
FIG. 6 is a perspective view of a gear box and output shaft of the actuator of FIGS. 4A-5.

FIG. 6 is a partial perspective view of the actuator 300 showing the output shaft 120 assembled with the gear box 114. As shown, the shaft 120 may include the shaft portion 124 that extends outward from the gearbox 114. Further, the elongated shaft portion 124 may include a flat portion 123. The flat portion 123 may be a non-rounded contour. The flat portion 123 may be any contour that differs from the other surrounding outer contour of the shaft portion 124. The shaft portion 124 may include a rounded portion 125. Thus there may be the flat portion 123 surrounded by the rounded portion 125. The flat portion 123 and the rounded portion 125 may extend longitudinally along the length of the shaft portion 124. The flat portion 123 and/or the rounded portion 125 may extend to the tip or proximal end of the shaft portion 124, as shown. Thus, the second attachment area 128 may include the flat portion 123 and the rounded portion 125. The first attachment area 126 may also include the flat portion 123 and the rounded portion 125, as shown. The rounded portion 125 at the second attachment area 128 may be threaded, etc., as described herein.

The shaft portion 124 may have a "D" cross-sectional shape, with a flat side on an otherwise rounded cross-section. In some embodiments, there may be two or more flat portions 123, for example two flat portions 123 located opposite each other about an axis of the shaft portion 124. A variety of other non-circular cross-section shapes may be implemented that will provide for transmission of rotation forces to parts that are supported on the shaft portion 124. The shaft portion 124 may be polygonal, segmented, have multiple flat segments separated by multiple rounded or non-flat segments, other contours, or combinations thereof. The shaft portion 124 may be shaped to correspond and mechanically engage with the worm gear 130, the opening 144 of the inner race 142 of the radial bearing 140, and/or one or more of the openings 156, 162 of the thrust bearing 150. In some embodiments, the shaft portion 124 and corresponding openings of the various parts thereon may have a circular or other rounded cross-sectional shape. The shaft portion 124 and corresponding openings of the various parts thereon may be welded together. For example, the shaft portion 124 and the worm gear 130, and/or other parts, may be welded together and with corresponding circular cross-sectional shapes.

Figure 7A:
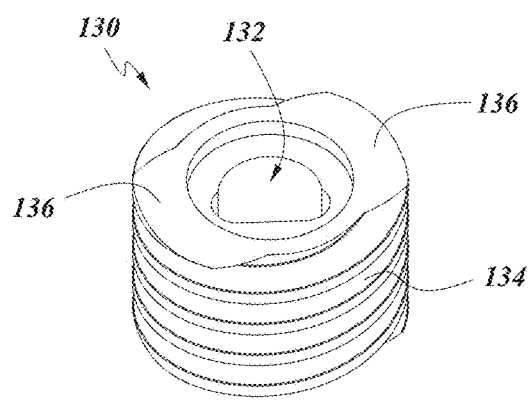
FIGS. 7A-7D are various views of a worm gear of the actuator of FIGS. 4A-5.
Figure 7B:
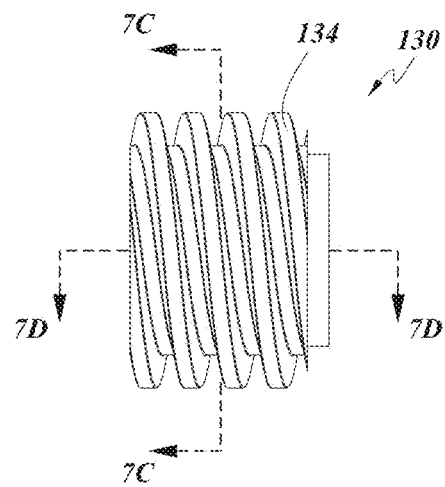
Figure 7C:
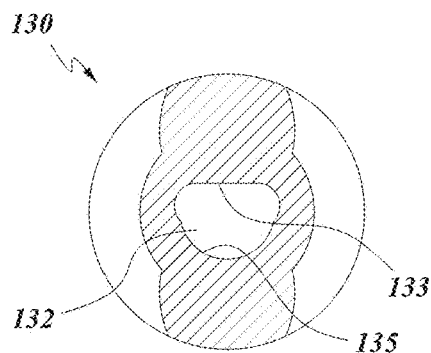
Figure 7D:
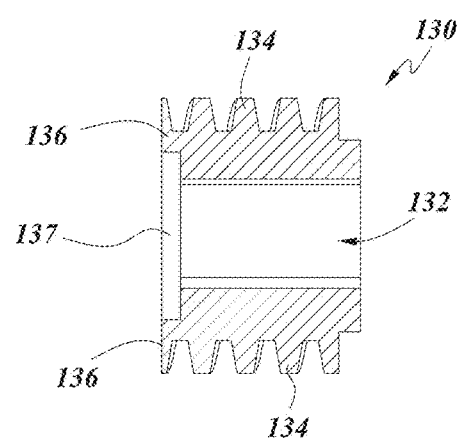

FIGS. 7A-7D are various views of the worm gear 130 of the actuator 300. FIG. 7A is a perspective view, FIG. 7B is a side view, FIG. 7C is a cross-sectional view as taken along the line 7C-7C (shown in FIG. 7B), and FIG. 7D is a cross-sectional view as taken along the line 7D-7D (shown in FIG. 7B). The worm gear 130 includes the opening 132 having a non-circular cross-sectional shape. As shown in FIG. 7C, the opening 132 may include a flat portion 133 surrounded by one or more rounded portions 135. The opening 132 may have any of the cross-sectional shapes as described with respect to the shaft portion 124, for example with respect to FIG. 6. When assembled together, the flat portion 133 and rounded portion 135 of the worm gear 130 may correspond to and engage with, respectively, the flat portion 123 and rounded portion 125 of the shaft portion 124. Rotation of the shaft 120 will thus transmit rotational forces to the worm gear 130 via the non-rounded engagement of the respective surfaces. For example, the flat portions 123, 133 will engage each other to transmit rotation from the shaft portion 124 to the worm gear 130. Similar shaped openings may be included with the opening 144 of the inner race 142 of the radial bearing 140, and/or one or more of the openings 156, 162 of the thrust bearing 150. In some embodiments, the shaft portion 124 and the worm gear 130 may be welded together, such that rotation of the shaft will rotate the worm gear via the welded connection. The shaft portion 124 and the worm gear 130 may have circular or other rounded cross-sectional shapes and be welded together, as described. Such welding may also be included in non-circular or non-rounded cross-sectional shapes, such as the "D" cross-section or others described herein, As shown in FIG. 7D, the worm gear 130 may include a recess 137 at an end thereof, for example at the distal end as assembled. The recess 137 may have an inner width that is greater than an inner width of the opening 132. The recess 137 may define a space on the end of the worm gear 130 to ensure that the distal end of the worm gear 130 does not contact the proximal end of the gearbox 114 (or proximal end of the motor 112 in embodiments not having the gearbox 114). The recess 137 may thus help define the space 170 located on the distal end of the worm gear 130 when assembled, as described herein, for example with respect to FIG. 5.

The recess 137 may be defined between one or more partial threads 136 at the end of the worm gear 130 that extend outwardly and radially away from an axis of the worm gear 130. The continuation of the spiral threads 134 become flat against a plane orthogonal to the axis of rotation. The partial threads 136 may be on the proximal and/or distal end of the worm gear 130. The recess 137 may be located on the proximal and/or distal end of the worm gear 130. The recess may allow for glue or weld overflow when assembling and/or manufacturing the shaft 120 and worm gear 130. In some embodiments, the recess 137 is located on the proximal end of the worm gear 130, and a spacer is used to orient the worm gear 130 against the distal end of the inner race 142 of the radial bearing 140. The spacer may be a thin, circular structure with an opening therethrough, e.g. similar to a washer.

Figure 8A:
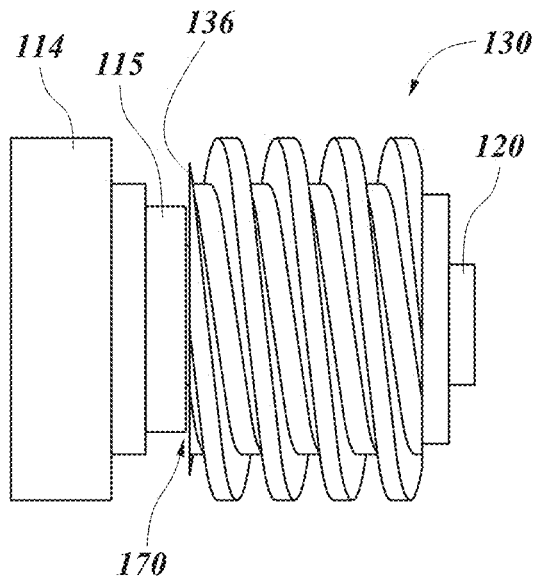
FIGS. 8A-8B are side and cross-section views, respectively, of an embodiment of a space between a worm gear and gearbox that may be implemented with the various actuators described herein.
Figure 8B:
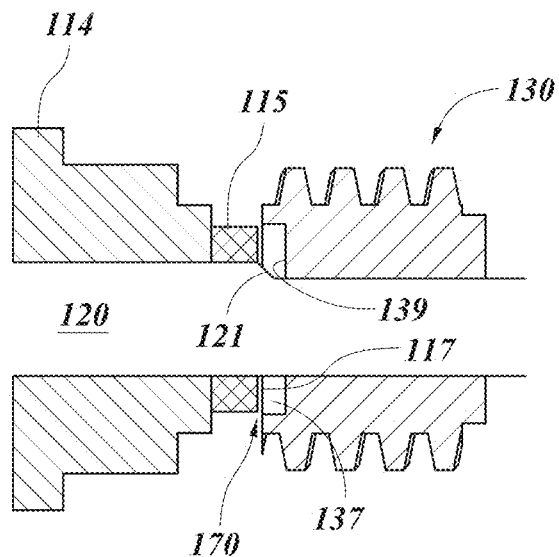

FIGS. 8A-8B are side and cross-section views, respectively, of another embodiment of the space 170 between the worm gear 130 and gearbox 114 that may be implemented with the various actuators described herein. The actuator, such as the actuator 300, may include a bushing 115 located at a proximal end of the gearbox 114. The bushing 115 may have a proximal-facing surface 117. The bushing 115 may have an outer width, e.g. outer diameter.

The shaft 120 may include a ramp 121 located at a longitudinal station along the length of the shaft 120. The ramp 121 may be on the shaft portion 124. The ramp 121 may be a projection extending radially outwardly from the shaft portion 124. The ramp 121 may be located at a proximal end of the bushing 115. The ramp 121 may be a transition zone of the shaft 120 where the shaft 120 changes from a circular cross-section to a non-circular cross-section. In some embodiments, the shaft portion 124 may have a circular cross-section on both sides of the ramp 121.

The worm gear 130 may have the recess 137 with a floor 139, which may be a distal-facing surface as oriented in the figure. The floor 139 partially forms the recess 137, such as a depth thereof. The floor 139 may be axially separated from the proximal-most end of the ramp 121. The floor 139 may not contact the ramp 121. The floor 139 may be located distally of the ramp 121.

The recess 137 may have a width, e.g. diameter. The width may extend between opposing inner walls of the recess 137, e.g. between opposing inner walls of the partial threads 136. The proximal-most end of the bushing, such as the surface 117, may be separated from a distal-most surface of the worm gear 130, such as the partial thread 136. The space 170 may exist axially between the worm gear 130 and the bushing 115, for example between the distal-most surface of the worm gear and the proximal-most surface of the bushing 115. In embodiments where there is no bushing 115, similar arrangements may be implemented between the gearbox 114 and the worm gear 130. The space 170 may have any of the sizes described herein, for example with respect to FIG. 5.

Figure 9A:
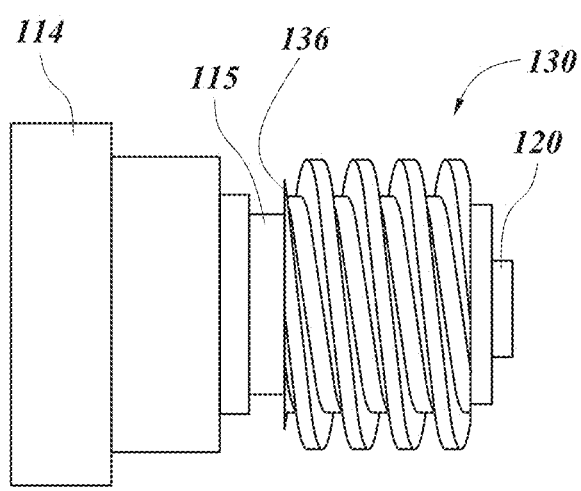
FIGS. 9A-9B are side and cross-section views, respectively, of another embodiment of a space between a worm gear and gearbox that may be implemented with the various actuators described herein.
Figure 9B:
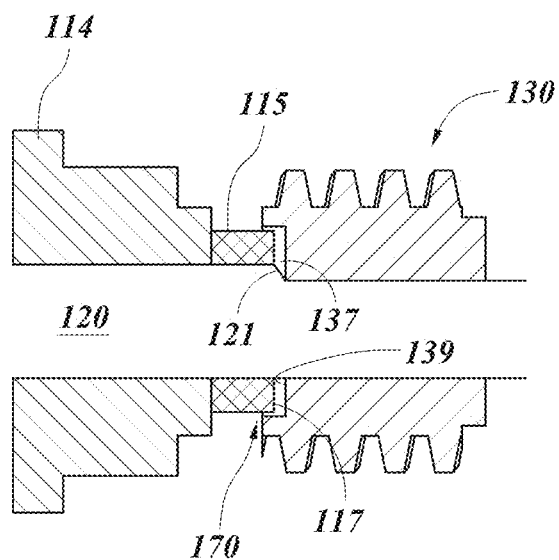

FIGS. 9A-9B are side and cross-section views, respectively, of another embodiment of the space 170 between the worm gear 130 and gearbox 114 that may be implemented with the various actuators described herein. The embodiment of the space 170 shown in FIGS. 9A-9B may have similar features as the embodiment of the space 170 shown in FIGS. 8A-8B, except as otherwise described. The embodiments shown in FIGS. 8A-9B may include any of the features and functions of the various parts as described herein, for instance for the worm gear 130, shaft 120, etc., for example as described with respect to any of FIGS. 3A-7D. The worm gear 130 may therefore have a circular or non-circular opening, the shaft 120 may have a circular and/or non-circular cross-sectional shape, etc.

As shown in FIGS. 9A-9B, the distal-most end of the worm gear 130 may be located distally of the proximal-most end of the bushing 115, such as the bushing surface 117. Thus, when assembled, an axial gap between the worm gear 130 and the bushing 115 may not be visible. However, there may still be an axial gap between the bushing surface 117 and the floor 139. The space 170 may further include a gap between radial-facing surfaces of the worm gear 130 and the bushing 115. The outer width of the bushing 115 may be smaller than the inner width of the recess 137. Thus the space 170 may be between an outer surface of the bushing 115 and an inner wall or surface of the recess 137. The space 170 may therefore include axial and radial gaps between the opposing parts.

The shaft ramp 121 may contact the floor 139 of the worm gear 130. The floor 139 may abut a proximal end of the ramp 121. The ramp 121 may be a limiting structural feature, such as stop, for axially locating the worm gear 130 on the shaft 120. The ramp 121 may limit travel of the worm gear 130 in the distal direction. The worm gear 130 may bottom out on the ramp 121 and/or other structural features of the shaft 120. The worm gear 130 may bottom out and contact the ramp 121 and/or other structural features of the shaft 120 and also be attached to the shaft 120 in one or more of any of the other attachment methods described herein, such as welding, bonding, etc. The ramp 121 or portions thereof may be located proximally of the distal-most surface of the worm gear 130 when assembled. In embodiments where there is no bushing 115, similar arrangements may be implemented between a proximal end of the gearbox 114 and the worm gear 130. The space 170 may have any of the dimensions described herein, for example with respect to FIG. 5, albeit in a radial direction.

In some embodiments, the worm gear 130 may radially contact the bushing 115 but still have an axial space 170 therebetween. For example, the respective radially opposing surfaces of the outer surface of the bushing 115 and the inner surfaces of the worm gear 130, such as the radially inward facing surfaces of the recess 137, may contact each other when assembled. These surfaces may form an interference, friction and/or other type fit between them when assembled. There may still be a space 170 between axially opposing surfaces of the bushing 115 and the worm gear 130, such as between the proximal-facing surface of the bushing 115 and the distal facing surface of the floor 139 of the worm gear 130. Thus the worm gear 130 may be radially supported but axially unguided by the bushing 115.

Figure 10A:
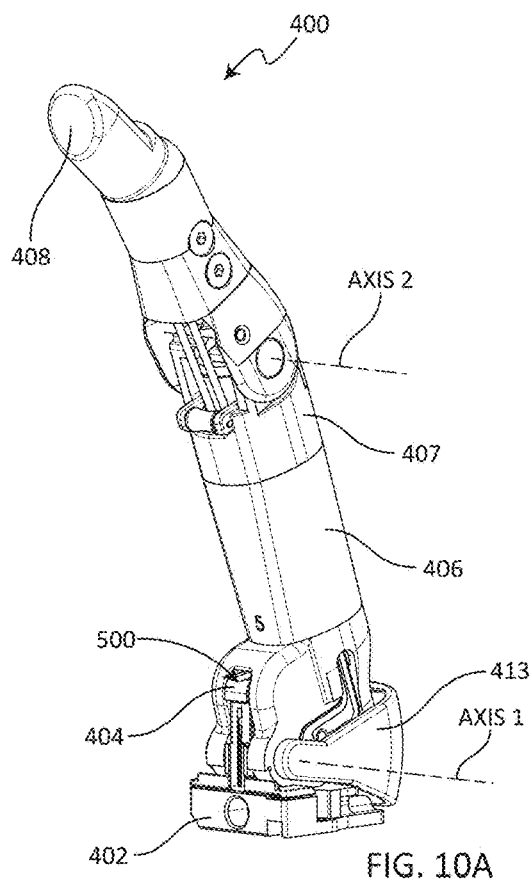
FIGS. 10A-10G are various views of another embodiment of a prosthetic digit having an actuator where the output shaft has a unibody worm gear.
Figure 10B:
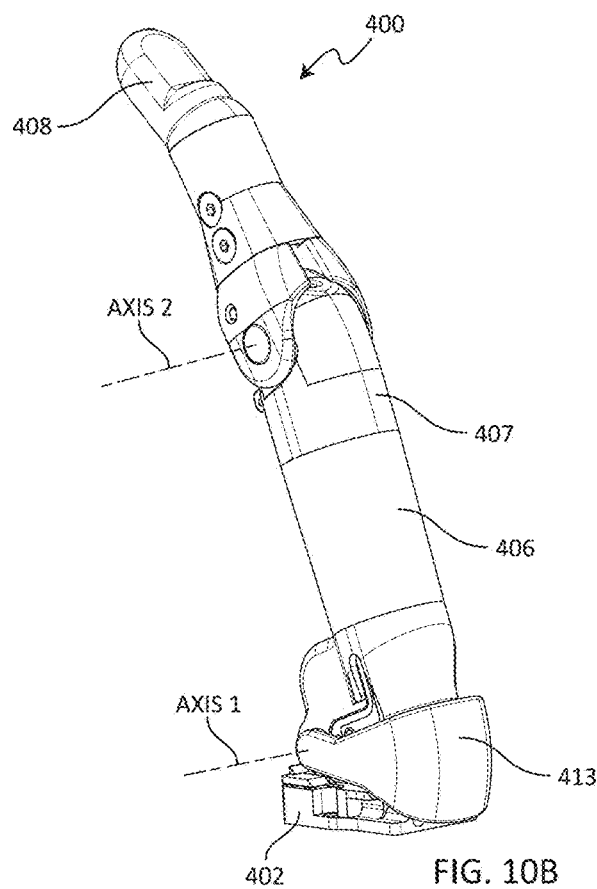
Figure 10C:
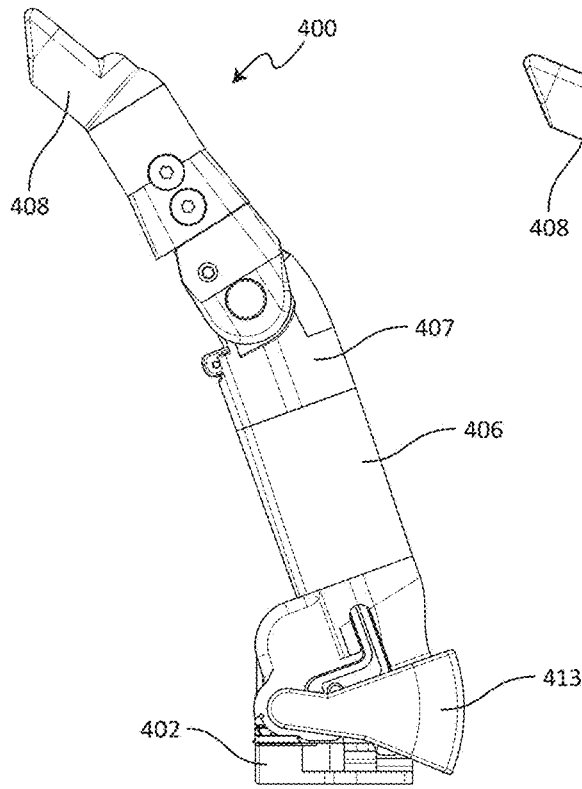
Figure 10D:
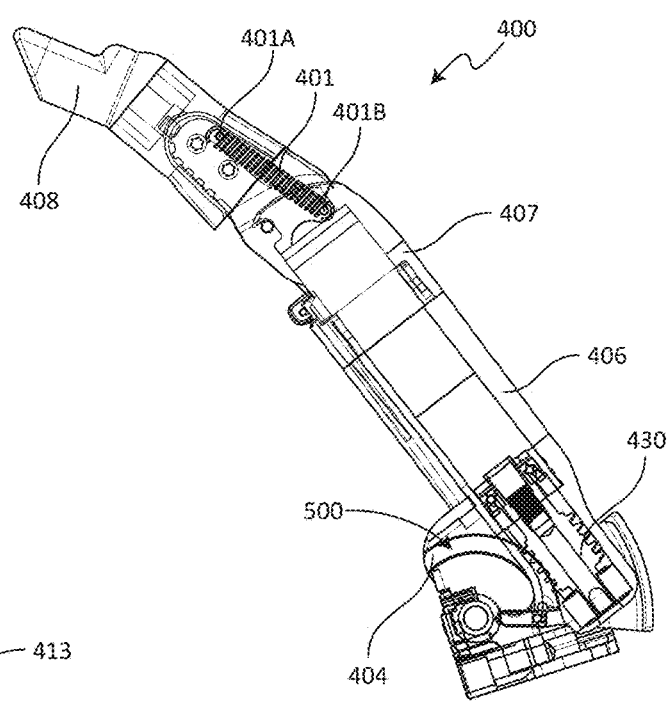
Figure 10E:
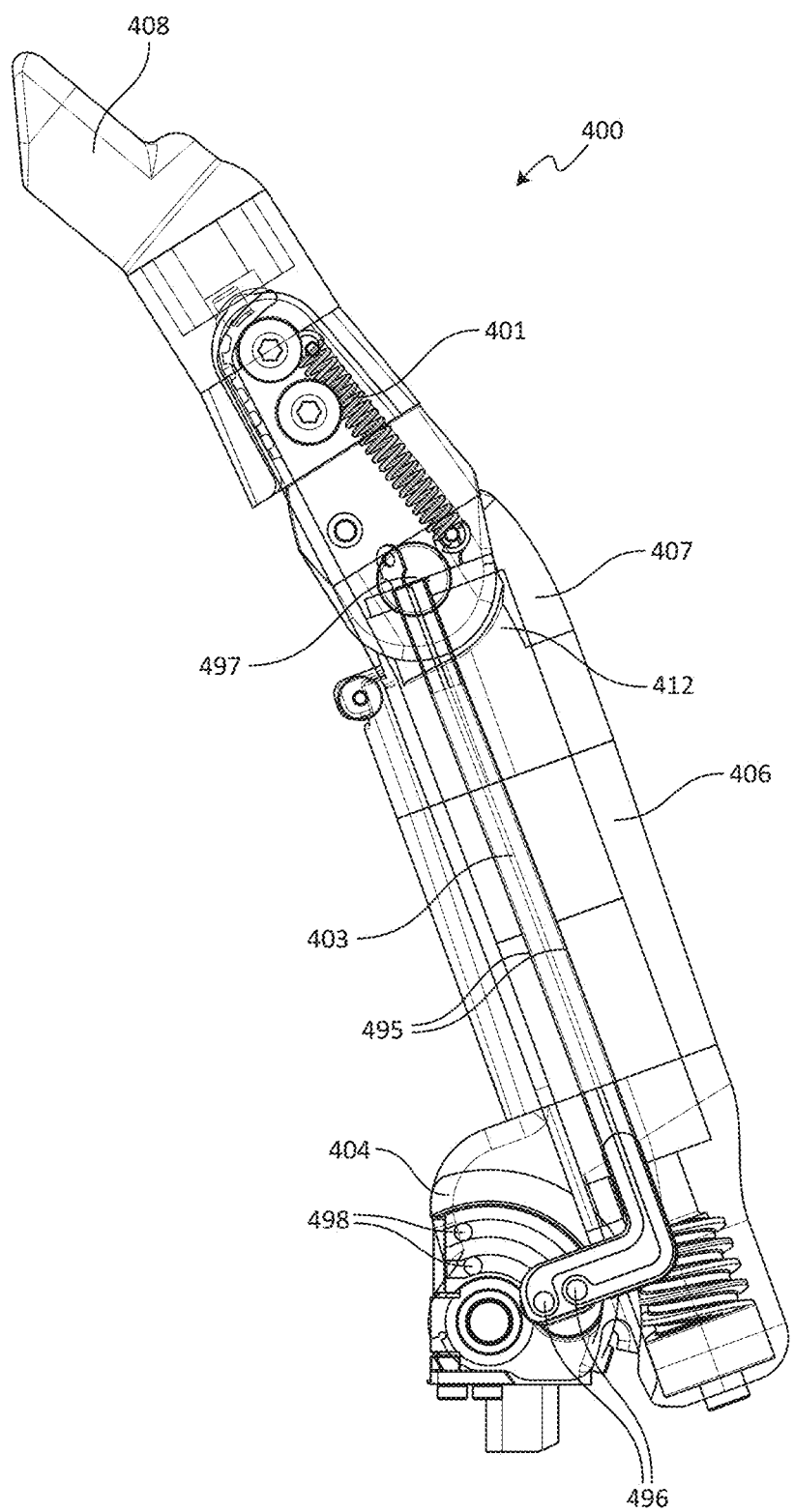
Figure 10G:
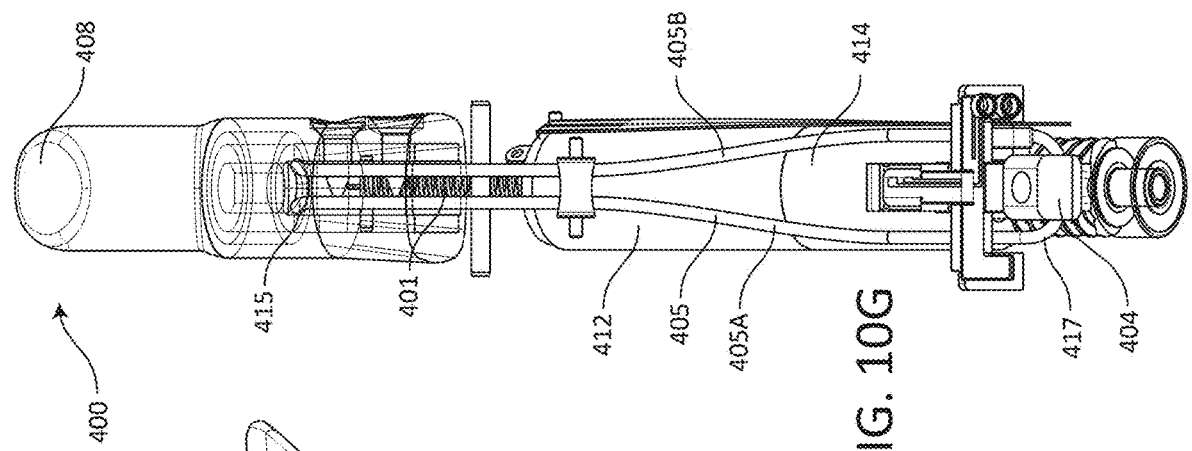
Figure 10F:
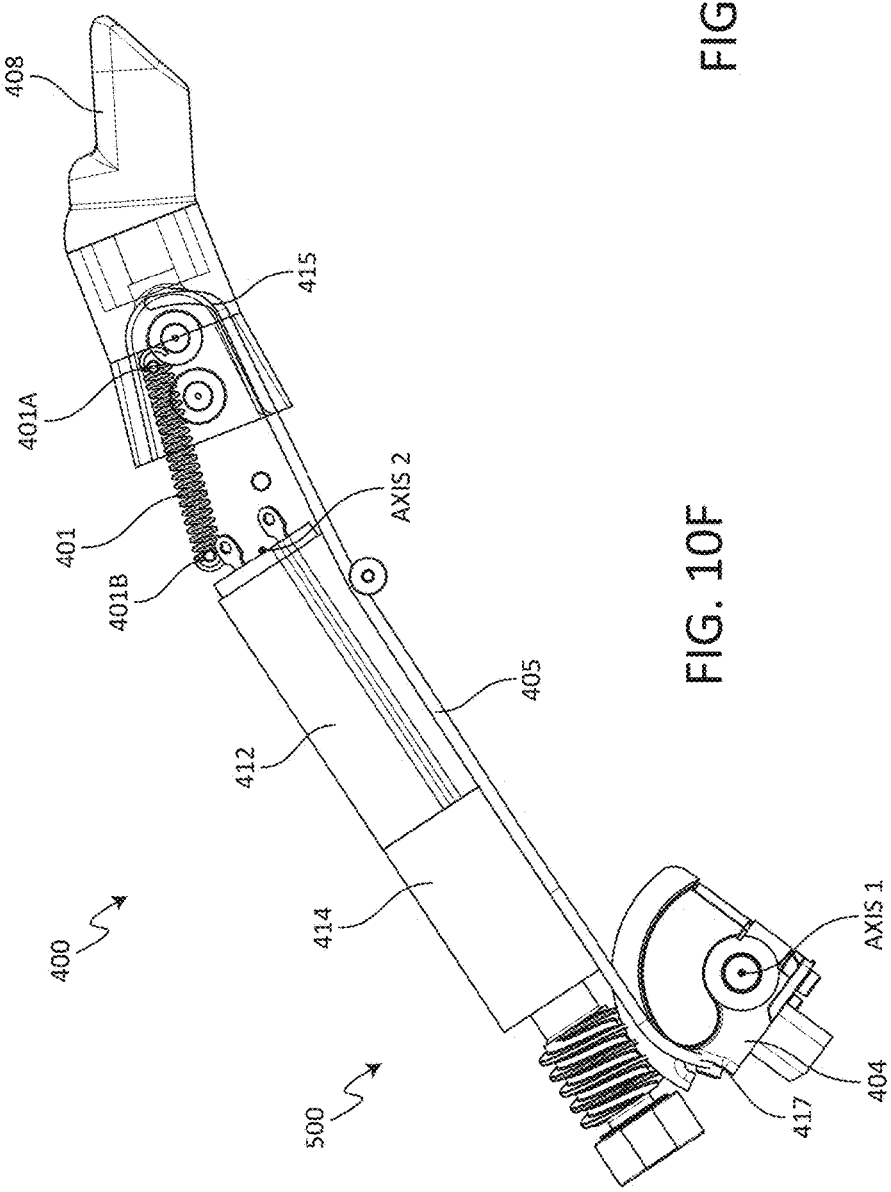

FIGS. 10A-10G are various views of another embodiment of a prosthetic digit 400 having an actuator 500 with an output shaft 420 having a unibody worm gear 430. FIG. 10A is a bottom perspective view, FIG. 10B is a top perspective view, FIG. 10C is a side view, FIG. 10D is a side cross-section view, FIG. 10E is a side view of the digit 400 with some components shown transparently for clarity, and FIGS. 10F and 10G are respectively a side view and a bottom perspective view of the digit 400 showing a tendon and with certain components hidden for clarity. The digit 400 and components thereof may have the same or similar features and/or functions as the digit 100 and respective components thereof, and vice versa, except as otherwise described herein.

The digit 400 includes a base 402, a worm wheel 404, a housing 406, a distal portion 407, a distal segment 408, a first rotational axis, a second rotational axis, and an actuator 500, which may have the same or similar features and/or functions as, respectively, the base 102, the worm wheel 104, the housing 106, the distal portion 107, the distal segment 108, the first rotational axis, the second rotational axis, and the actuator 300 of the digit 100.

The digit 400 further includes a fairing 413. The fairing 413 covers the proximal end of the digit 400. The fairing 413 may be attached to the digit 400 about the axis 1. The fairing 413 may attach at two opposite sides of the digit 400 at the axis 1. The fairing 413 may extend along opposite sides of the digit 400 and around the digit 400 from one attachment point to the other. The fairing 413 may be spaced apart from the proximal end of the digit 400 such that the digit 400 can rotate underneath the fairing 413. The fairing 413 provides structural protection of the rotating digit 400, for example the rotating proximal end of the digit 400. The fairing 413 may be stationary. In some embodiments, the fairing 413 may rotate, for example about the axis 1. The fairing 413 may be removable and re-attachable, for example with a friction fit about the digit 400 or by other suitable mechanical attachment means. The fairing 413 may be removed to access the proximal end of the digit 400 for instance to adjust a proximal end 428 of the output shaft 420, as further described herein, for example with respect to FIG. 12.

As shown in FIG. 10D, the actuator 500 includes a worm gear 430 and a worm wheel 404, which may have the same or similar features and/or functions as, respectively, the worm gear 130 and the worm wheel 104. The worm gear 130 is unibody with the output shaft 420, as further described. The threaded worm gear 430 is rotated and in response moves along the outer threaded, rounded contour of the worm wheel 404, as described herein with respect to the gear 130 and wheel 104.

As further shown in FIG. 10D, the digit 400 includes an extension spring 401. The spring 401 extends from the distal portion 407 to the distal segment 408. A proximal end of the spring 401 may attach to the distal segment 408 and a distal end of the spring 401 may attach to the distal segment 408. The spring 401 may attach to a first rod 401A of the distal segment 408 and a second rod 401B of the distal portion 407. The spring 401 provides a biasing rotational force on the distal segment 408 of the digit 400 that rotationally biases the distal segment 408 to straighten out. The spring 401 may thus "pull" on the distal segment 408 toward the distal portion 407.

FIGS. 10D and 10F-10G show the digit 400 including a tendon 405. For clarity, certain structures of the digit 400 are hidden in FIGS. 10D and 10F-10G, including the housing of the distal portion 407, the proximal housing 406, and the fairing 413.

The tendon 405 is a tether or wire, which may be inelastic or substantially inelastic. In some embodiments, the tendon 405 may be elastic. The tendon 405 extends from or near the worm wheel 404, along the housing 406, and to a distal end of the distal portion 407. The tendon 405 may further extend to the distal segment 408. The tendon 405 may effectively shorten or lengthen the distance between the segments as the digit 400 rotates to cause the distal segment 408 to rotate relative to the proximal segment of the digit 400 having the housing 406. As the digit 400 rotates to open (or clockwise as oriented in FIGS. 10D and 10E), the tendon 405 may effectively lengthen and allow the distal segment 408 to straighten out via the extension spring 401. Conversely, as the digit 400 rotates to close (or counterclockwise as oriented in FIGS. 10D and 10E), the tendon 405 may effectively shorten pulling on the distal segment 408 to create a torque of the distal segment 408 about its pivot point with the proximal segment, thereby causing the distal segment 408 to also rotate counterclockwise relative to the proximal segment and toward the base 402.

As shown in FIGS. 10F and 10G, the tendon 405 extends from the worm wheel 404 along the length of the digit 400 to the distal segment 408. The tendon 405 has a proximal end 417 that attaches to the worm wheel 404. A set screw or other mechanical mechanism may secure the proximal end 417 to the worm wheel 404. The tendon 405 has a distal end 415 that attaches to or wraps around a portion of the distal segment 408. The tendon 405 may be continuous and include a first segment 405A and a second segment 405B extending from the worm wheel 404 to the distal segment 408, as shown in FIG. 10G. The tendon 405 may be secured at the proximal end 417 and extend along the first and second segments 405A, 405B to the distal end 415. The first segment 405A and the second segment 405B may extend from the worm wheel 404, distally underneath the proximal segment of the digit 400, along a pulley or rod, and to the distal segment 408. The distal end 415 may wrap around a rod or other attachment in the distal segment 408. The tendon 405 may extend a distance away from the axis 2 to create a torque about the axis 2 when rotating closed. The tendon 405 may be an inelastic or substantially inelastic member.

The tendon 405 and the extension spring 401 operate to cause the proximal and distal segments of the digit 400 to rotate open and closed as the worm gear 430 travels along the worm wheel 404. The extension spring 401 biases the digit 400 to open. The tendon 405 pulls on the digit to close. The digit 400 may be rotated open or closed by the actuator 500. In some embodiments, the digit 400 may be rotated open and closed by external forces, such as by an object exerting an external force on the digit 400.

When the actuator 500 causes a closing rotation, the worm gear 430 travels along the worm wheel in the clockwise direction as oriented in FIG. 10F to rotate the gearbox 414 clockwise about the Axis 1. The fixed proximal end 417 of the tendon 405 effectively shortens the length of the tendon 405, pulling on the distal end 415 of the tendon 405 to cause the distal segment 408 of the digit 400 to rotate clockwise in a closing direction about the Axis 2. As the digit 400 rotates to close, the extension spring 401 extends and stores a potential compressive restoring force to bias the digit 400 toward the open position. Similar action of the spring 401 and tendon 405 may operate when the digit 400 is rotated closed by an external force.

When the actuator 500 causes an opening rotation, the worm gear 430 travels along the worm wheel in the counterclockwise direction as oriented in FIG. 10F to rotate the gearbox 414 counterclockwise about the Axis 1. The fixed proximal end 417 of the tendon 405 effectively lengthens the length of the tendon 405, allowing the stored potential force of the spring 401 to cause the distal segment 408 of the digit 400 to rotate counterclockwise in an opening direction about the Axis 2. As the digit 400 rotates to open, the extension spring 401 contracts and releases the potential compressive restoring force. The open position may include the distal segment 408 forming an extended position that is parallel or near parallel to the housing 406 of the proximal segment of the digit 400. Similar action of the spring 401 and tendon 405 may operate when the digit 400 is rotated open by an external force.

As shown in FIG. 10E, the digit 400 includes an electrical support 403. The support 403 extends from the worm wheel 404, along the housing 406, and to a distal end of a motor 412. A pair of electrical leads 495 extend from respective proximal connections 496 to distal connections 497. The proximal connections 496 are electrically connected with conductive surfaces 498 of the worm wheel 404. The distal connections 497 are electrically connected with conductive surfaces of the motor 412. Power is supplied from a battery in the prosthetic hand to which the digit 400 is connected to the motor 412 via the electrical leads 495 as described. The proximal connections 496 may move over the conductive surfaces 498 as the digit 400 rotates to continuously provide power to the motor 412 during digit 400 rotation.

Figure 11:
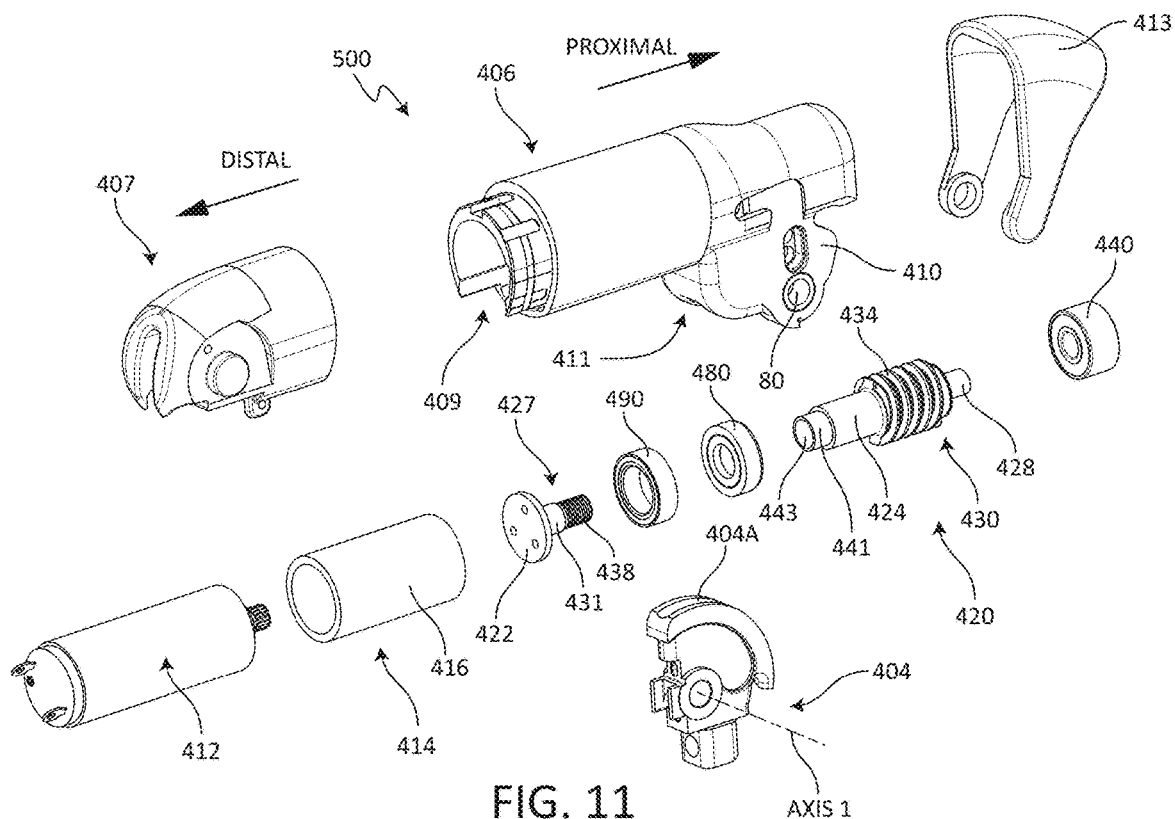
FIG. 11 is a partial exploded view of the actuator of the prosthetic digit of FIGS. 10A-10G.
Figure 12:
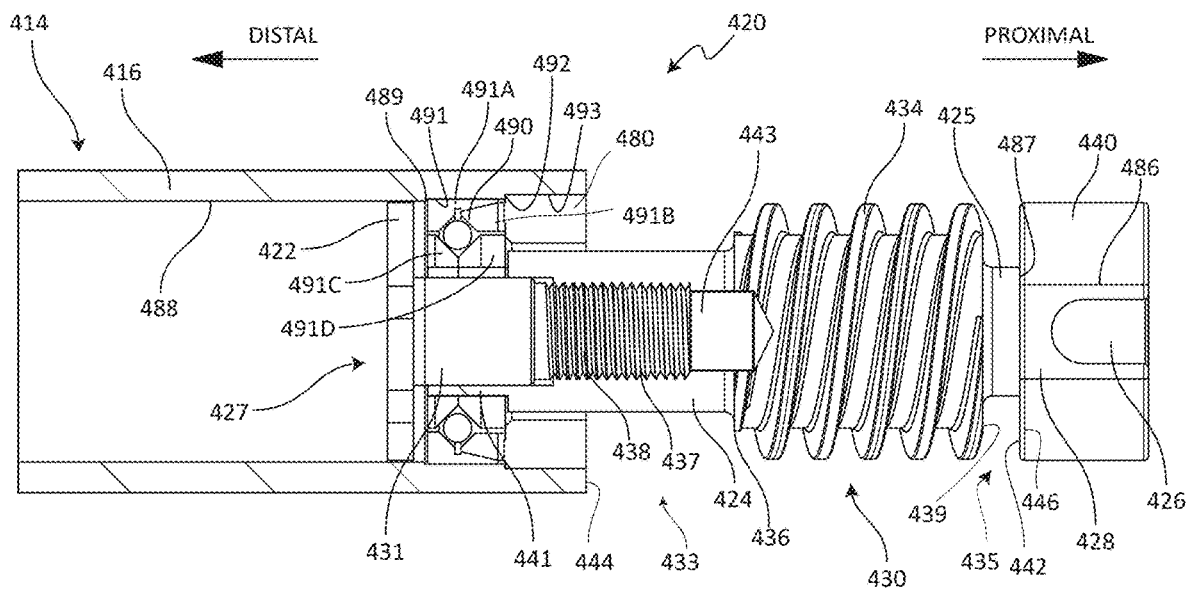
FIG. 12 is a cross-section view of the output shaft of the actuator from FIGS. 10A-11.

FIG. 11 is a partial exploded view of the actuator 500. FIG. 12 is a side cross-section view of the actuator 500 showing only some components for clarity, including an output shaft 420. The actuator 500 includes the motor 412 and a gearbox 414, which may have the same or similar features, respectively, as the motor 112 and the gearbox 114 of the digit 100. The actuator 500 may cause rotation of a prosthetic digit as described herein for other digits. Thus, the worm gear 430 may rotate about its own longitudinal axis to travel along teeth 404A of the worm wheel 404 and rotate about the axis 1, to thereby cause the proximal segment of the prosthetic digit, e.g. the housing 406, the motor 412, and/or the gearbox 414, to rotate about the axis 1 as well. The housing 406 and distal portion 407 define an opening 409 therethrough in which the motor 412, gearbox 414, and shaft 420 are located. The housing 406 includes a clevis 410 defining a space 411 therein and the opening 80, which may have the same or similar features and/or functions as, respectively, the clevis 410, space 411 and the opening 80 of the digit 100.

The digit 400 further includes an output carrier 427 having a larger diameter head 422 with a smaller diameter shaft 431 extending from the head 422. The carrier 422 may be part of a gearbox or set of gears within the gearbox 414. The gearbox 414 via the carrier 422 and other gears therein may transmit rotation from the motor 412 to the output shaft 420. The proximal end of the carrier 422 has an external thread 438.

The output shaft 420 includes a rounded distal portion 424 and a rounded proximal portion 425. In between the distal and proximal portions 424, 425 is the worm gear 430 having threads 434. The threads 434 may have the same or similar features and/or functions as the threads 134 of the digit 100. The worm gear 430 and the shaft portions 424, 425 are unibody. Thus the worm gear 430 and the shaft portions 424, 425 are a single, monolithic piece. The worm gear 430 and the shaft portions 424, 425 may be machined from the same piece of material, or they may be welded together, or they may be 3D-printed as a single piece. Other suitable fabrication methods may be employed to create the unibody shaft 420. The worm gear 430 may therefore not move axially relative to the shaft portions 424, 425. There may not be any guidances or other structures contacting either axial side of the worm gear 430. For example, in the illustrated example of FIG. 12, there is a first gap 433 defined between a distal-facing side 436 of a distal end of the threads 434 of the worm gear 430 and a proximal-facing side 444 of a proximal end of the gearbox housing 416, and a second gap 435 defined between a distal-facing side 446 of a distal end of the radial bearing 440 and a proximal-facing side 439 of a proximal end of the threads 434 of the worm gear 430.

The shaft 420 further includes a distal end 441. The distal end 441 extends distally from the distal shaft portion 424. The distal end 441 has a stepped-down (smaller) outer diameter than the distal shaft portion 424. The distal end 441 and the distal portion 424 may have a similar inner diameter to receive the carrier shaft 431 therein. The distal end 441 may also be unibody with the other features of the shaft 420. The distal end 441 and the portions 424, 425 may have circular cross-sections.

The distal end 441 may define a distal opening 443 therethrough. The opening 443 may extend into the distal portion 424. The opening 443 may have internal threads 437 along a portion thereof. The internal threads 437 may be located proximally of the distal end 441. The opening 443 may extend distally of the threads 437, for example to a location within a distal portion of the external threads 434 of the shaft 420. This is one example configuration, and the internal threads 437 and the extent of the opening 443 may be located axially along the shaft 420 in other locations. In some embodiments, the opening 443 may extend completely through the shaft 420. As shown, the shaft 420 includes a proximal opening 426 that protrudes slightly into the proximal end of the shaft 420, and the shaft 420 is solid between the two openings 443, 426.

The opening 443 of the shaft 420 may receive the shaft 431 of the carrier 427 therein. The external threads 438 of the carrier shaft 431 may mate with corresponding internal threads 437 of the shaft 420. The carrier 427 and the shaft 420 may be rotated relative to each other to cause the threads 437, 438 to engage and thereby engage the shaft 420 with the carrier 427.

The carrier head 422 and part of the carrier shaft 431 are located within the housing 416 of the gearbox 414. The gearbox 414 includes a first diameter section 488 and a second relatively larger diameter section 491 with a radial step 489 therebetween. Similarly, the gearbox 414 includes the second diameter section 491 and a third relatively larger diameter section 493 with a radial step 492 therebetween. Thus the third diameter section 493 is wider than the second diameter section 491 which is wider than the first diameter section 488.

The actuator 500 further includes a distal bearing 490. The distal bearing 490 is a 4-point contact bearing that can take up both radial and axial loads. In some embodiments, other types of bearings or combinations of different types of bearings may be used for the distal bearing 490. The distal bearing 490 is located within the housing of the gearbox 414 within the second diameter section 491 with a distal end of the bearing 490 resting on the step 489.

The distal bearing 490 may have one or more outer races and one or more inner races. As shown, first and second outer races 491A, 491B of the bearing 490 contact the inner sidewall of the gearbox 414 housing 416 and first and second inner races 491C, 491D of the bearing 490 contact the outer surfaces of the distal end 441 of the shaft 420. The inner races 491C, 491D rotate with the shaft 420 relative to the outer races 491A, 491B. The outer races 491A, 491B may be stationary relative to the gearbox housing 416 as the inner races 491C, 491D rotate. The first outer race 491A may be located distally of the second outer race 491B. The first outer race 491A may contact the step 489, which may prevent axial travel of the bearing 490 in the distal direction. The second outer race 491B may contact and be compressed by the preload ring 480. The second outer race 491B may be rotationally stationary relative to the preload ring 480 and/or the housing 416.

The second inner race 491D may be located proximally of the first inner race 491C. The second inner race 491D may contact the step 432 of the shaft 420. The step 432 may be a radially extending outer surface connecting the relatively smaller outer diameter distal end 441 and the relatively larger outer diameter distal portion 424 of the output shaft 420.

The proximal end of the bearing 490 may be located slightly distally of the radial step 492 such that a bearing preload ring 480 contacts the proximal end of the bearing 490 to axially secure the bearing 490 within the gearbox 414. The ring 480 may contact one or more outer races of the bearing 490 such that the one or more inner races of the bearing 490 can rotate free of interference from the ring 480. The ring 480 is secured and constrained by the housing of the gearbox 414. A proximal end of the ring 480 may align with the proximal end of the gearbox 414.

The actuator 500 includes a proximal bearing 440. The bearing 440 may be a radial bearing configured to take up radial loads at the proximal end of the shaft 420. The bearing 440 is located at the proximal end 428 of the shaft 420. The bearing 440 is located on a relatively smaller diameter section 486 of the proximal end 428 with respect to the proximal portion 425 of the shaft 420. A radial step 487 is located between the proximal portion 425 and the section 486. The bearing 440 is axially located next to the step 487. One or more shims 442 may be used between the bearing 440 and the step 487 to finely axially align the bearing 440.

Various modifications to the implementations described in this disclosure can be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. An actuator for a prosthetic digit, the actuator comprising:
   a gearbox housing;
   a motor;
   an output shaft extending proximally along a rotation axis, wherein the motor is in mechanical communication with the output shaft and is configured to cause a rotation of the output shaft about the rotation axis, the output shaft including a worm gear that is unibody with and axially fixed on the output shaft proximally of the gearbox housing, the worm gear comprising threads, wherein a first gap is defined between a distal-facing side of a distal end of the threads of the worm gear and a proximal-facing side of a proximal end of the gearbox housing;
   a radial bearing supported along the output shaft proximally of the worm gear, wherein a second gap is defined between a distal-facing side of a distal end of the radial bearing and a proximal-facing side of a proximal end of the threads of the worm gear, and the radial bearing comprising an inner race in mechanical communication with an outer race;
   a 4-point contact bearing located within the gearbox housing at a distal end of the output shaft distally of the worm gear and distally of the first gap, the 4-point contact bearing comprising at least one outer race and at least one inner race, wherein the at least one outer race contacts a step on an inner sidewall of the gearbox housing that prevents distal translation of the 4-point contact bearing, and the at least one inner race contacts the distal end of the output shaft and is configured to rotate with the output shaft relative to the at least one outer race, such that rotation of the output shaft rotates the at least one inner race about the rotation axis, and the at least one outer race is axially compressed by the gearbox housing and a preload ring, the preload ring being disposed within the gearbox housing proximally of the 4-point contact bearing and contacting only a single proximal-facing surface of the 4-point contact bearing; and
   a worm wheel configured to be attached with a prosthetic hand, wherein the worm wheel is in mechanical communication with the threads of the worm gear such that rotation of the worm gear about the rotation axis causes the worm gear to travel along an arcuate outer perimeter of the worm wheel to thereby rotate the gearbox housing about the worm wheel.

2. The actuator of claim 1, further comprising a carrier shaft extending proximally and configured to engage the output shaft to mechanically transmit rotation from the motor via the gearbox to the output shaft.

3. The actuator of claim 1, further comprising a carrier shaft, wherein the output shaft comprises an internal opening extending axially at least partially therethrough and is configured to at least partially receive the carrier shaft therein.

4. The actuator of claim 3, wherein the internal opening comprises internal threads and the carrier shaft comprises external threads configured to engage the internal threads.

5. The actuator of claim 1, further comprising a gearbox, wherein the motor is configured to rotate the output shaft via the gearbox.

6. The actuator of claim 1, wherein the at least one inner race comprises two inner races and the at least one outer race comprises two outer races.

7. The actuator of claim 6, wherein the two inner races contact and rotate with the output shaft, and the two outer races are axially compressed by the housing and a preload ring.

8. An actuator for a prosthetic digit, the actuator comprising:
   a gearbox housing;
   a motor;
   an output shaft having a worm gear that is unibody with the output shaft, the output shaft extending proximally along a rotation axis, wherein the motor is in mechanical communication with the output shaft and is configured to cause a rotation of the output shaft about the rotation axis, wherein the worm gear is located proximally of the gearbox housing, the worm gear comprising a threads, and wherein a first gap is defined between a distal-facing side of a distal end of the threads of the worm gear and a proximal-facing side of a proximal end of the gearbox housing;
   a first bearing located at a proximal end of the output shaft proximally of the worm gear, wherein a second gap is defined between a distal-facing side of a distal end of the first bearing and a proximal-facing side of a proximal end of the threads of the worm gear;
   a second bearing located within the gearbox housing at a distal end of the output shaft distally of the worm gear and distally of the first gap, the second bearing comprising at least one outer race and at least one inner race, wherein the at least one outer race contacts and rotates with the output shaft, and the at least one outer race is axially compressed by the gearbox housing and a preload ring, the preload ring being disposed within the gearbox housing proximally of the second bearing and contacting a proximal-facing surface of the second bearing; and
   a worm wheel configured to be attached with a prosthetic hand, wherein the worm wheel is in mechanical communication with the threads of the worm gear such that rotation of the worm gear about the rotation axis causes the worm gear to travel along the worm wheel to cause the gearbox housing and motor to rotate about the worm wheel.

9. The actuator of claim 8, the gearbox housing further comprising an inward step on an inner surface, wherein the inward step prevents axial movement of the second bearing in a distal direction.

10. The actuator of claim 8, further comprising a carrier shaft extending proximally and configured to engage the output shaft to mechanically transmit rotation to the output shaft.

11. The actuator of claim 8, further comprising a carrier shaft, wherein the output shaft comprises an internal opening extending axially at least partially therethrough and is configured to at least partially receive the carrier shaft therein.

12. The actuator of claim 11, wherein the internal opening comprises internal threads and the carrier shaft comprises external threads configured to engage the internal threads.

13. The actuator of claim 8, wherein the first bearing is a radial bearing comprising an inner race in mechanical communication with an outer race.

14. The actuator of claim 8, wherein the second bearing is a 4-point contact bearing comprising at least one outer race and at least one inner race, wherein the at least one outer race contacts a step on an inner sidewall of the gearbox housing that prevents distal translation of the 4-point contact bearing, and the at least one inner race contacts the distal end of the output shaft and is configured to rotate relative to the at least one outer race, such that rotation of the output shaft rotates the at least one inner race about the rotation axis.

15. The actuator of claim 8, wherein rotation of the worm gear about the rotation axis causes the worm gear to travel along an arcuate outer perimeter of the worm wheel.

16. The actuator of claim 8, further comprising a gearbox within the gearbox housing and in mechanical communication with the motor.

17. A prosthetic digit comprising:
 an actuator comprising:
  a gearbox housing;
  a motor;
  an output shaft having a worm gear that is unibody with the output shaft, the output shaft extending proximally along a rotation axis, wherein the motor is in mechanical communication with the output shaft and is configured to cause a rotation of the output shaft about the rotation axis, wherein the worm gear is located proximally of the gearbox housing, the worm gear comprising a threads, and wherein a first gap is defined between a distal-facing side of a distal end of the threads of the worm gear and a proximal-facing side of a proximal end of the gearbox housing;
  a first bearing located at a proximal end of the output shaft proximally of the worm gear, wherein a second gap is defined between a distal-facing side of a distal end of the first bearing and a proximal-facing side of a proximal end of the threads of the worm gear;
  a second bearing located within the gearbox housing at a distal end of the output shaft distally of the worm gear and distally of the first gap, the second bearing comprising at least one outer race and at least one inner race, wherein the at least one outer race contacts and rotates with the output shaft, and the at least one outer race is axially compressed by the gearbox housing and a preload ring, the preload ring being disposed within the gearbox housing proximally of the second bearing and contacting a proximal-facing surface of the second bearing; and
  a worm wheel configured to be attached with a prosthetic hand, wherein the worm wheel is in mechanical communication with the threads of the worm gear such that rotation of the worm gear about the rotation axis causes the worm gear to travel along the worm wheel to cause the gearbox housing and motor to rotate about the worm wheel.

18. The prosthetic digit of claim 17, the gearbox housing further comprising an inward step on an inner surface, wherein the inward step prevents axial movement of the second bearing in a distal direction.

19. The prosthetic digit of claim 17, wherein the actuator further comprises a carrier shaft extending proximally and configured to engage the output shaft to mechanically transmit rotation to the output shaft.

20. The prosthetic digit of claim 17, wherein the actuator further comprises a carrier shaft, wherein the output shaft comprises an internal opening extending axially at least partially therethrough and is configured to at least partially receive the carrier shaft therein.

\* \* \* \* \*

UNITED STATES PATENT AND TRADEMARK OFFICE
CERTIFICATE OF CORRECTION

PATENT NO. : 11,931,270 B2
APPLICATION NO. : 17/098045
DATED : March 19, 2024
INVENTOR(S) : Rodrigo Mercader Rivera et al.

Page 1 of 1

It is certified that error appears in the above-identified patent and that said Letters Patent is hereby corrected as shown below:

In the Specification

Column 2, Line 50, delete "as actuator" and insert -- an actuator --.

Column 17, Line 4, delete "herein," and insert -- herein, --.

In the Claims

Column 26, Line 29, in Claim 8, delete "wherein the at least one outer race contacts" and insert -- wherein the at least one inner race contacts --.

Column 28, Lines 3-4, in Claim 17, delete "wherein the at least one outer race contacts" and insert -- wherein the at least one inner race contacts --.

Signed and Sealed this
Second Day of July, 2024

Katherine Kelly Vidal
*Director of the United States Patent and Trademark Office*